(12) United States Patent
Kojima

(10) Patent No.: US 10,910,548 B2
(45) Date of Patent: Feb. 2, 2021

(54) ULTRASONIC DEVICE, ULTRASONIC PROBE, ULTRASONIC APPARATUS, AND ULTRASONIC DEVICE MANUFACTURING METHOD

(71) Applicant: Seiko Epson Corporation, Tokyo (JP)

(72) Inventor: Chikara Kojima, Matsumoto (JP)

(73) Assignee: Seiko Epson Corporation

( * ) Notice: Subject to any disclaimer, the term of this patent is extended or adjusted under 35 U.S.C. 154(b) by 901 days.

(21) Appl. No.: 15/428,479

(22) Filed: Feb. 9, 2017

(65) Prior Publication Data

US 2017/0244022 A1 Aug. 24, 2017

(30) Foreign Application Priority Data

Feb. 22, 2016 (JP) ................. 2016-031393

(51) Int. Cl.
| | |
|---|---|
| *A61B 8/14* | (2006.01) |
| *H01L 41/053* | (2006.01) |
| *H01L 41/00* | (2013.01) |
| *H01L 41/047* | (2006.01) |
| *G01S 7/52* | (2006.01) |
| *A61B 8/00* | (2006.01) |
| *B06B 1/06* | (2006.01) |

(52) U.S. Cl.
CPC ............ *H01L 41/0475* (2013.01); *A61B 8/14* (2013.01); *A61B 8/4427* (2013.01); *A61B 8/4483* (2013.01); *A61B 8/54* (2013.01); *B06B 1/0622* (2013.01); *B06B 1/0644* (2013.01); *G01S 7/52079* (2013.01); *H01L 41/053* (2013.01)

(58) Field of Classification Search
CPC .......................... H01L 41/047; H01L 41/0475
See application file for complete search history.

(56) References Cited

U.S. PATENT DOCUMENTS

| | | | | |
|---|---|---|---|---|
| 9,079,220 | B2 * | 7/2015 | Nakamura | .......... H01L 41/0825 |
| 9,987,663 | B2 * | 6/2018 | Kojima | ................ B06B 1/0622 |
| 2007/0157731 | A1 | 7/2007 | Okuda et al. | |
| 2015/0258573 | A1 | 9/2015 | Kojima | |

FOREIGN PATENT DOCUMENTS

| | | |
|---|---|---|
| JP | 2000-023288 A | 1/2000 |
| JP | 2007-189303 A | 7/2007 |
| JP | 2011-255024 A | 12/2011 |
| JP | 2015-118028 A | 6/2015 |
| JP | 2015-188208 A | 10/2015 |

\* cited by examiner

*Primary Examiner* — Thomas M Dougherty
*Assistant Examiner* — Karen B Addison
(74) *Attorney, Agent, or Firm* — Hamess, Dickey & Pierce, P.L.C.

(57) ABSTRACT

An ultrasonic device includes: an element substrate including an ultrasonic transducer and a first connection electrode connected to the ultrasonic transducer; a reinforcing plate that is bonded to the element substrate to reinforce the element substrate; and a second connection electrode provided on the reinforcing plate. The first and second connection electrodes are connected to each other in a bonding portion between the element substrate and the reinforcing plate.

6 Claims, 15 Drawing Sheets

ULTRASONIC DEVICE, ULTRASONIC PROBE, ULTRASONIC APPARATUS, AND ULTRASONIC DEVICE MANUFACTURING METHOD

CROSS-REFERENCE TO RELATED APPLICATIONS

The entire disclosure of Japanese Patent Application No. 2016-031393 filed Feb. 22, 2016 is expressly incorporated by reference herein.

BACKGROUND

1. Technical Field

The present invention relates to an ultrasonic device, an ultrasonic probe, an ultrasonic apparatus, and an ultrasonic device manufacturing method.

2. Related Art

An ultrasound probe having an ultrasonic wave transmitting and receiving unit including a diaphragm, which has a driving layer formed of a piezoelectric material, and a support member, which supports the diaphragm and has an opening at a position corresponding to the diaphragm, is known (for example, refer to JP-A-2011-255024).

The ultrasonic probe includes a through silicon via substrate as a sealing member disposed on a side (back surface side) of the driving layer opposite to the support member. The through silicon via substrate and the support member are bonded to each other by anodic bonding, and vacuum space is formed on the back surface side of the diaphragm.

On the through silicon via substrate, a through electrode and a solder bump are formed at positions facing the driving layer. The solder bump is pressed against an electrode layer forming the driving layer by pressure at the time of bonding the support member and the through silicon via substrate to each other. Accordingly, the electrode layer on the driving layer side is connected to the through electrode through the solder bump. As a result, the electrode layer on the driving layer side is communicably connected to a signal processing circuit unit for driving the ultrasonic wave transmitting and receiving unit.

In the configuration disclosed in JP-A-2011-255024, however, the ultrasonic wave transmitting and receiving unit receives the pressing force from the solder bump. Therefore, since it is not possible to obtain an ultrasonic wave transmitting and receiving unit having desired performance, there is a possibility that the reliability will be lowered. That is, there is a possibility that the piezoelectric performance of the piezoelectric body will be lowered by the distortion of the driving layer and accordingly the transmission and reception performance (transmission sensitivity (transmission output) or reception sensitivity) of the ultrasonic wave transmitting and receiving unit will be lowered. In addition, there is a possibility that the natural frequency of the diaphragm will be changed by the distortion and accordingly the frequency characteristics of the ultrasonic wave transmitting and receiving unit will be changed. If the pressing force from the bump was large, there is also a possibility that the ultrasonic wave transmitting and receiving unit will be damaged. For example, cracking may occur in the driving layer or the support member.

SUMMARY

An advantage of some aspects of the invention is to provide a highly reliable ultrasonic device, ultrasonic probe, and ultrasonic apparatus and an ultrasonic device manufacturing method.

An ultrasonic device according to an application example of the invention includes: an element substrate that includes an ultrasonic transducer and a first connection electrode connected to the ultrasonic transducer; a reinforcing plate that is bonded to the element substrate to reinforce the element substrate; and a second connection electrode provided on the reinforcing plate. The first and second connection electrodes are connected to each other in a bonding portion between the element substrate and the reinforcing plate.

In the application example, the first connection electrode connected to the ultrasonic transducer and the second connection electrode provided on the reinforcing plate are electrically connected to each other in the bonding portion between the element substrate and the reinforcing plate. That is, in the application example, in the bonding portion between the element substrate and the reinforcing plate, an electrode can be pulled out from the element substrate side to the reinforcing plate side. Therefore, it is possible to mount wiring lines on the second connection electrode provided on the reinforcing plate. Therefore, since the stress due to the mounting of wiring lines is applied to the reinforcing plate, it is possible to suppress the application of the stress to the element substrate. As a result, it is possible to suppress the distortion of the element substrate.

As described above, in a case where a bump electrode for connecting the first and second connection electrodes to each other is provided at a position different from the bonding portion so as to be pressed against the first connection electrode or the second connection electrode, the element substrate is distorted by the pressing force from the bump electrode. For this reason, there is a possibility that the performance of the ultrasonic transducer will be lowered or the element substrate will be damaged.

In contrast, in the application example, in a bonding portion where the reinforcing plate is bonded to the element substrate, the first and second connection electrodes are connected to each other. Therefore, as in a case where a bump electrode is provided, it is possible to suppress the stress applied to the element substrate. As a result, it is possible to suppress the lowering of the performance of the ultrasonic transducer or damage to the element substrate.

As described above, it is possible to provide a highly reliable ultrasonic device including an ultrasonic transducer having desired characteristics.

In the ultrasonic device according to the application example, it is preferable that the ultrasonic transducer includes a piezoelectric element.

In the application example with this configuration, an ultrasonic transducer includes a piezoelectric element. In such a configuration, since the distortion of the element substrate can be suppressed, it is possible to suppress the occurrence of a situation in which the piezoelectric layer of the piezoelectric element is distorted according to the distortion of the element substrate and the piezoelectric performance is lowered. Therefore, even in a configuration in which the ultrasonic transducer includes a piezoelectric element, it is possible to provide a highly reliable ultrasonic device.

In the ultrasonic device according to the application example, it is preferable that the element substrate has a substrate body portion, in which an opening is formed, and a vibration film provided in the substrate body portion so as to close the opening and that the piezoelectric element is provided at a position, which overlaps the opening, on a surface of the vibration film not facing the opening when viewed from a thickness direction of the element substrate.

In the application example with this configuration, the element substrate has the substrate body portion and the vibration film that closes the opening provided in the substrate body portion. Then, the piezoelectric element is provided at a position, which overlaps the opening, on the side of the vibration film not facing the opening. In such an ultrasonic device, the vibration film vibrates according to the driving of the piezoelectric element, and ultrasonic waves are transmitted from the opening. In addition, when the vibration film is vibrated by the ultrasonic waves that have propagated toward the vibration film from the opening side, the vibration of the vibration film is detected by the piezoelectric element.

Incidentally, in such a configuration, for example, by forming an acoustic matching layer, which has intermediate acoustic impedance between the acoustic impedance of a measurement target such as a living body and the acoustic impedance of the ultrasonic device, within the opening, reflection on the interface between the measurement target and the ultrasonic device is suppressed. Accordingly, it is possible to suppress a reduction in measurement accuracy. On the other hand, if the thickness of the element substrate is large, the depth of the opening is increased. As the thickness of the acoustic matching layer increases, the amount of attenuation of ultrasonic waves is increased. For this reason, there is a possibility that the ultrasonic wave transmission and reception performance will be lowered. However, as described above, in a known configuration, if the element substrate is made thin, the strength of the element substrate is reduced. For this reason, there is a possibility that distortion is likely to occur or the element substrate is likely to be damaged.

In contrast, in the application example with the configuration described above, since it is possible to suppress the stress applied to the element substrate, it is possible to suppress the occurrence of distortion of the element substrate while reducing the depth of the opening by making the element substrate thin. Accordingly, it is possible to improve the ultrasonic wave transmission and reception performance.

In the ultrasonic device according to the application example, it is preferable that the reinforcing plate has a protruding portion that protrudes from the element substrate when viewed from the thickness direction of the element substrate and that a part of the second connection electrode is provided in the protruding portion.

In the application example with this configuration, the reinforcing plate has a protruding portion that protrudes from the element substrate in the plan view, and a part of the second connection electrode is provided in the protruding portion. In such a configuration, the second connection electrode can be pulled out to a position (for example, an end of the protruding portion) on the reinforcing plate away from the bonding portion between the element substrate and the reinforcing plate. Therefore, for example, when making a connection to a circuit board using a wiring material, such as an FPC, it is possible to separate the wiring position from the element substrate. As a result, it is possible to suppress the distortion of the element substrate more reliably.

In the ultrasonic device according to the application example, it is preferable that the bonding portion surrounds a region where the ultrasonic transducer of the element substrate is provided.

In the application example with this configuration, the bonding portion is disposed so as to surround a region where the ultrasonic transducer is provided, and the element substrate is bonded to the reinforcing plate by the bonding portion. In such a configuration, compared with a configuration in which apart of the periphery of a region where the ultrasonic transducer is provided is bonded to the reinforcing plate, it is possible to firmly fix the element substrate to the reinforcing plate. Therefore, it is possible to suppress the distortion of the element substrate more reliably.

In addition, as described above, in a case where the piezoelectric element is formed on the reinforcing plate side of the element substrate, it is possible to seal the space where the piezoelectric element is formed by the element substrate, the reinforcing plate, and the bonding portion. Therefore, since it is possible to suppress the permeation of water into the space where the piezoelectric element is formed, it is possible to suppress the deterioration of the piezoelectric element.

In the ultrasonic device according to the application example, it is preferable that the element substrate and the reinforcing plate are bonded to each other using an adhesive.

In the application example with this configuration, the element substrate and the reinforcing plate are bonded to each other using an adhesive. In such a configuration, since bonding between the element substrate and the reinforcing plate can be easily performed, it is possible to improve the manufacturing efficiency.

An ultrasonic probe according to an application example of the invention includes: an ultrasonic device; and a housing in which the ultrasonic device is housed. The ultrasonic device includes: an element substrate that includes an ultrasonic transducer and a first connection electrode connected to the ultrasonic transducer; a reinforcing plate that is bonded to the element substrate to reinforce the element substrate; and a second connection electrode provided on the reinforcing plate. The first and second connection electrodes are connected to each other in a bonding portion between the element substrate and the reinforcing plate.

In the application example, the first connection electrode connected to the ultrasonic transducer and the second connection electrode provided on the reinforcing plate are electrically connected to each other in the bonding portion between the element substrate and the reinforcing plate. In such a configuration, in the same manner as in the application example relevant to the ultrasonic device described above, an electrode can be pulled out from the element substrate side to the reinforcing plate side in the bonding portion between the element substrate and the reinforcing plate. Therefore, it is possible to mount wiring lines on the second connection electrode of the reinforcing plate. Therefore, since the stress due to the mounting of wiring lines is applied to the reinforcing plate, it is possible to suppress the application of the stress to the element substrate. As a result, it is possible to suppress the distortion of the element substrate.

In addition, as described above, compared with a configuration in which the first and second connection electrodes are connected to each other using a bump electrode, it is possible to suppress the stress applied to the element substrate. Therefore, it is possible to suppress the lowering of the performance of the ultrasonic transducer or damage to the element substrate.

As described above, it is possible to provide a highly reliable ultrasonic probe including an ultrasonic transducer having desired characteristics.

An ultrasonic apparatus according to an application example of the invention includes: an ultrasonic device; and a control unit that controls the ultrasonic device. The ultrasonic device includes: an element substrate that includes an ultrasonic transducer and a first connection electrode connected to the ultrasonic transducer; a reinforcing plate that is bonded to the element substrate to reinforce the element substrate; and a second connection electrode provided on the reinforcing plate. The first and second connection electrodes are connected to each other in a bonding portion between the element substrate and the reinforcing plate.

In the application example, the first connection electrode connected to the ultrasonic transducer and the second connection electrode provided on the reinforcing plate are electrically connected to each other in the bonding portion between the element substrate and the reinforcing plate. In such a configuration, in the same manner as in the application example relevant to the ultrasonic device described above, an electrode can be pulled out from the element substrate side to the reinforcing plate side in the bonding portion between the element substrate and the reinforcing plate. Therefore, it is possible to mount wiring lines on the second connection electrode of the reinforcing plate. Therefore, since the stress due to the mounting of wiring lines is applied to the reinforcing plate, it is possible to suppress the application of the stress to the element substrate. As a result, it is possible to suppress the distortion of the element substrate.

In addition, as described above, compared with a configuration in which the first and second connection electrodes are connected to each other using a bump electrode, it is possible to suppress the stress applied to the element substrate. Therefore, it is possible to suppress the lowering of the performance of the ultrasonic transducer or damage to the element substrate.

As described above, it is possible to provide a highly reliable ultrasonic apparatus including an ultrasonic transducer having desired characteristics.

An ultrasonic device manufacturing method according to an application example of the invention includes: forming an element substrate including an ultrasonic transducer and a first connection electrode connected to the ultrasonic transducer; forming a reinforcing plate for reinforcing the element substrate; and bonding the element substrate and the reinforcing plate to each other. The forming of the element substrate includes forming the ultrasonic transducer and forming the first connection electrode in at least a bonding portion between the element substrate and the reinforcing plate. The forming of the reinforcing plate includes forming the second connection electrode in at least the bonding portion. In the bonding, the element substrate and the reinforcing plate are bonded to each other while making the first and second connection electrodes in contact with each other in the bonding portion.

In the ultrasonic device manufactured according to the manufacturing method of the application example, the first connection electrode connected to the ultrasonic transducer and the second connection electrode provided on the reinforcing plate are electrically connected to each other in the bonding portion between the element substrate and the reinforcing plate. In such a configuration, in the same manner as in the application example relevant to the ultrasonic device described above, an electrode can be pulled out from the element substrate side to the reinforcing plate side in the bonding portion between the element substrate and the reinforcing plate. Therefore, it is possible to mount wiring lines on the second connection electrode of the reinforcing plate. Therefore, since the stress due to the mounting of wiring lines is applied to the reinforcing plate, it is possible to suppress the application of the stress to the element substrate. As a result, it is possible to suppress the distortion of the element substrate.

In addition, as described above, compared with a configuration in which the first and second connection electrodes are connected to each other using a bump electrode, it is possible to suppress the stress applied to the element substrate. Therefore, it is possible to suppress the lowering of the performance of the ultrasonic transducer or damage to the element substrate.

As described above, it is possible to manufacture a highly reliable ultrasonic device including an ultrasonic transducer having desired characteristics.

In the ultrasonic device manufacturing method according to the application example, it is preferable to further include processing the element substrate. It is preferable that the forming of the element substrate includes forming a vibration film in a substrate body portion. Preferably, in the forming of the first connection electrode, the substrate body portion is exposed by removing a part of the vibration film, and the first connection electrode is formed along an exposed portion where at least the substrate body portion is exposed. Preferably, in the processing of the element substrate, the exposed portion and the first connection electrode formed along the exposed portion are removed.

In the application example, in the forming of the element substrate, a part of the first connection electrode is formed in the exposed portion that is exposed by removing the vibration film formed in the substrate body portion. Then, in the processing of the element substrate, the exposed portion where a part of the first connection electrode is formed and the first connection electrode formed along the exposed portion are removed. By removing the exposed portion in this manner, it is possible to form a plurality of element substrates simultaneously from the long substrate.

Usually, the first connection electrode is formed of a material (for example, a conductive material, such as metal) different from the material of the element substrate or the reinforcing plate having an insulation property. Accordingly, it is possible to selectively remove the first connection electrode. Since this is easy, it is possible to improve the production efficiency.

In the ultrasonic device manufacturing method according to the application example, it is preferable that, in the processing of the element substrate, the exposed portion is removed from an opposite side of the first connection electrode and then the first connection electrode formed along the exposed portion is removed.

In the application example, the exposed portion is removed from the side opposite to a side where the first connection electrode is provided. Then, the first connection electrode formed along the exposed portion is removed. That is, a portion of the first connection electrode overlapping the exposed portion in a plan view as viewed from the thickness direction of the element substrate is removed.

For example, in the case of removing the exposed portion by etching, a portion of the first connection electrode formed along the exposed portion can be used as an etching stopper layer. Therefore, in the case of forming a plurality of element substrates simultaneously from the long substrate as described above, it is possible to suppress the occurrence of a situation in which a member, which is located on a side opposite to the exposed portion with respect to the first connection electrode, comes in contact with an etching material to deteriorate.

In the ultrasonic device manufacturing method according to the application example, it is preferable that, in the forming of the first connection electrode, when the element substrate and the reinforcing plate are bonded to each other, the exposed portion is formed at a position of the substrate body portion overlapping the second connection electrode in a plan view as viewed from a thickness direction of the element substrate.

In the application example, in a plan view as viewed from the thickness direction of the element substrate, when the element substrate and the reinforcing plate are bonded to each other, the exposed portion is formed at a position overlapping the second connection electrode. In such a configuration, in the processing of the element substrate, the second connection electrode can be exposed by removing the exposed portion and the first connection electrode formed along the exposed portion.

In the ultrasonic device manufacturing method according to the application example, it is preferable that, in the bonding, the element substrate and the reinforcing plate are bonded to each other using an adhesive and the adhesive is provided at a position where at least the second connection electrode is covered on the reinforcing plate.

In the application example, the element substrate and the reinforcing plate are bonded to each other using an adhesive, and the adhesive is provided at a position where at least the second connection electrode is covered on the reinforcing plate. In such a configuration, in the bonding, the element substrate and the reinforcing plate can be bonded to each other, and the second connection electrode can be covered with an adhesive. Accordingly, when removing the first connection electrode formed along the exposed portion by processing the element substrate after the bonding, it is possible to use the adhesive as a protective film of the second connection electrode. Therefore, it is possible to suppress the deterioration of the second connection electrode.

BRIEF DESCRIPTION OF THE DRAWINGS

The invention will be described with reference to the accompanying drawings, wherein like numbers reference like elements.

DESCRIPTION OF EXEMPLARY EMBODIMENTS

Hereinafter, an embodiment of the invention will be described.

Figure 1:
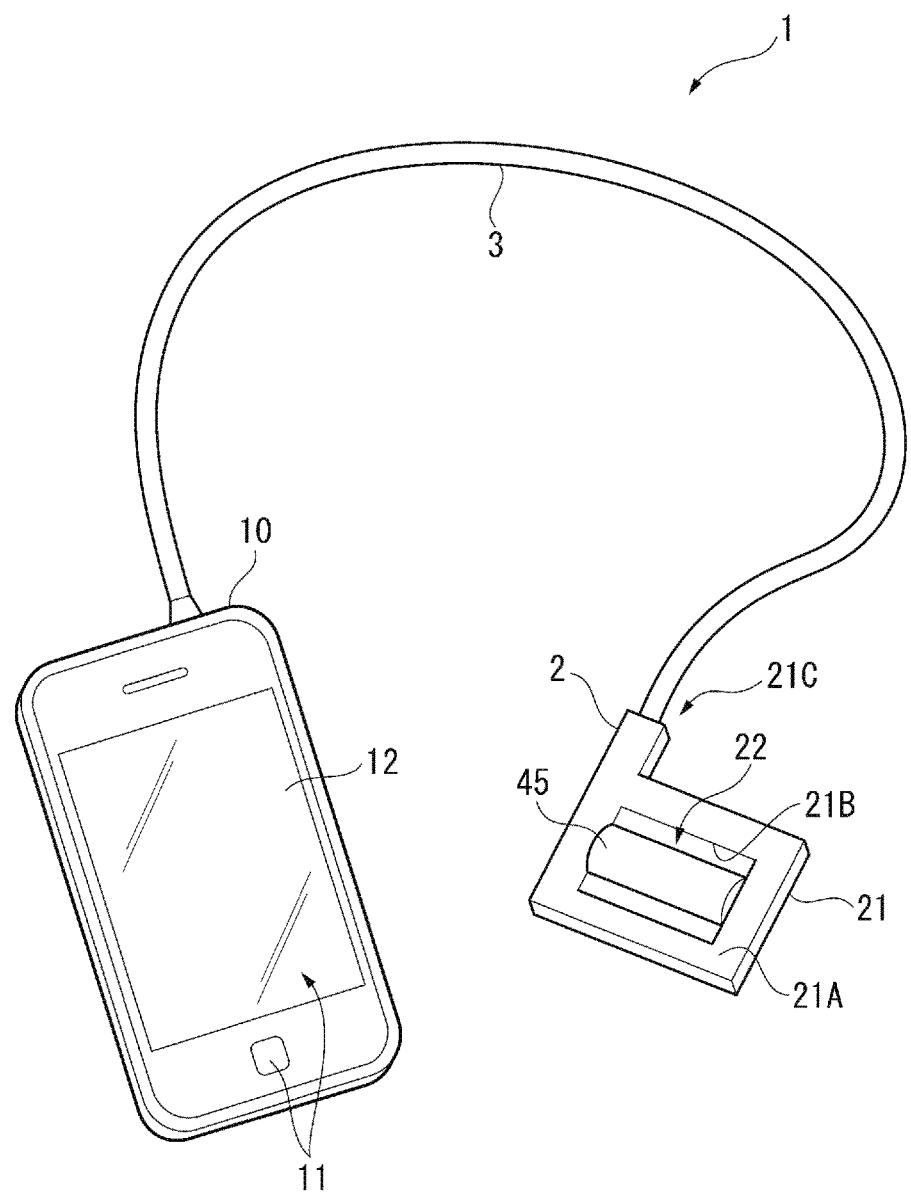
FIG. 1 is a diagram showing the schematic configuration of an ultrasonic measurement apparatus.
Figure 2:
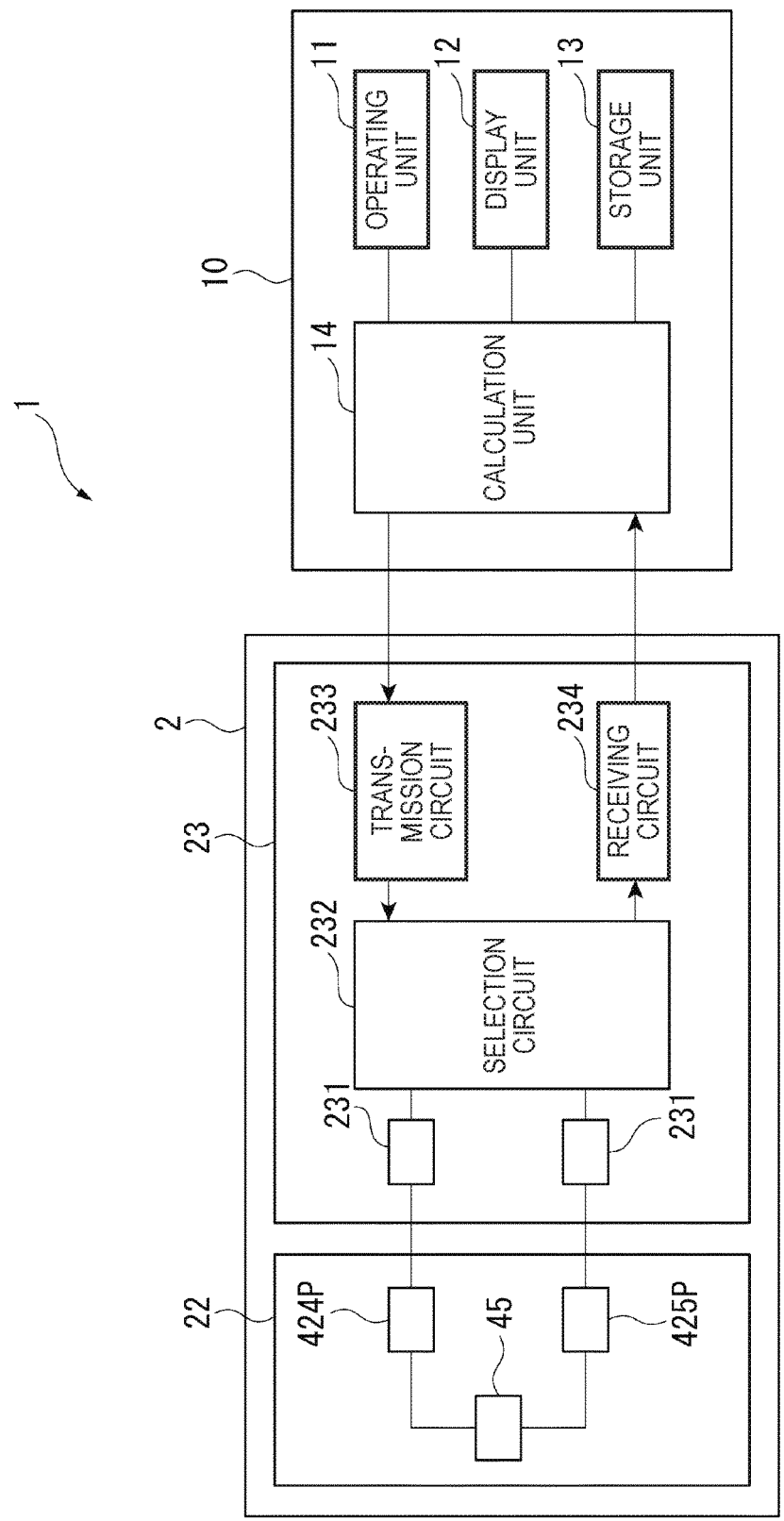
FIG. 2 is a block diagram showing the schematic configuration of the ultrasonic measurement apparatus.

FIG. 1 is a diagram showing the schematic configuration of an ultrasonic measurement apparatus 1 of the present embodiment. FIG. 2 is a block diagram showing the schematic configuration of the ultrasonic measurement apparatus 1.

As shown in FIG. 1, the ultrasonic measurement apparatus 1 (ultrasonic apparatus) of the present embodiment includes an ultrasonic probe 2 and a control device 10 (control unit) that is electrically connected to the ultrasonic probe 2 through a cable 3.

In the ultrasonic measurement apparatus 1, the ultrasonic probe 2 is brought into contact with the surface of the living body (for example, a human body), ultrasonic waves are transmitted to the inside of the object (for example, a living body) from the ultrasonic probe 2, ultrasonic waves reflected by the organ in the living body are received by the ultrasonic probe 2, and, for example, an internal tomographic image in the living body is obtained or the state of the organ in the living body (for example, a blood flow) is measured based on the received signal.

Configuration of Ultrasonic Probe

The ultrasonic probe 2 includes a housing 21 (refer to FIG. 1), an ultrasonic device 22 housed in the housing 21, and a circuit board 23 in which a driver circuit for controlling the ultrasonic device 22 and the like are provided.

Configuration of Housing

As shown in FIG. 1, the housing 21 is formed in a rectangular box shape in a plan view, for example. A sensor window 21B is provided on one surface (sensor surface 21A) perpendicular to the thickness direction, so that a part of the ultrasonic device 22 is exposed. A passage hole 21C of the cable 3 is provided in a part of the housing 21 (in the example shown in FIG. 1, on a side surface), and the cable 3 is connected to the circuit board 23 by being inserted to the inside of the housing 21 through the passage hole 21C. In addition, a gap between the cable 3 and the passage hole 21C is filled with, for example, a resin material. Accordingly, waterproofness is ensured.

In the present embodiment, an example of the configuration is shown in which the ultrasonic probe 2 and the control device 10 are connected to each other using the cable 3. However, without being limited thereto, for example, the ultrasonic probe 2 and the control device 10 may be connected to each other by wireless communication, or various components of the control device 10 may be provided in the ultrasonic probe 2.

Configuration of Ultrasonic Device

Figure 3:
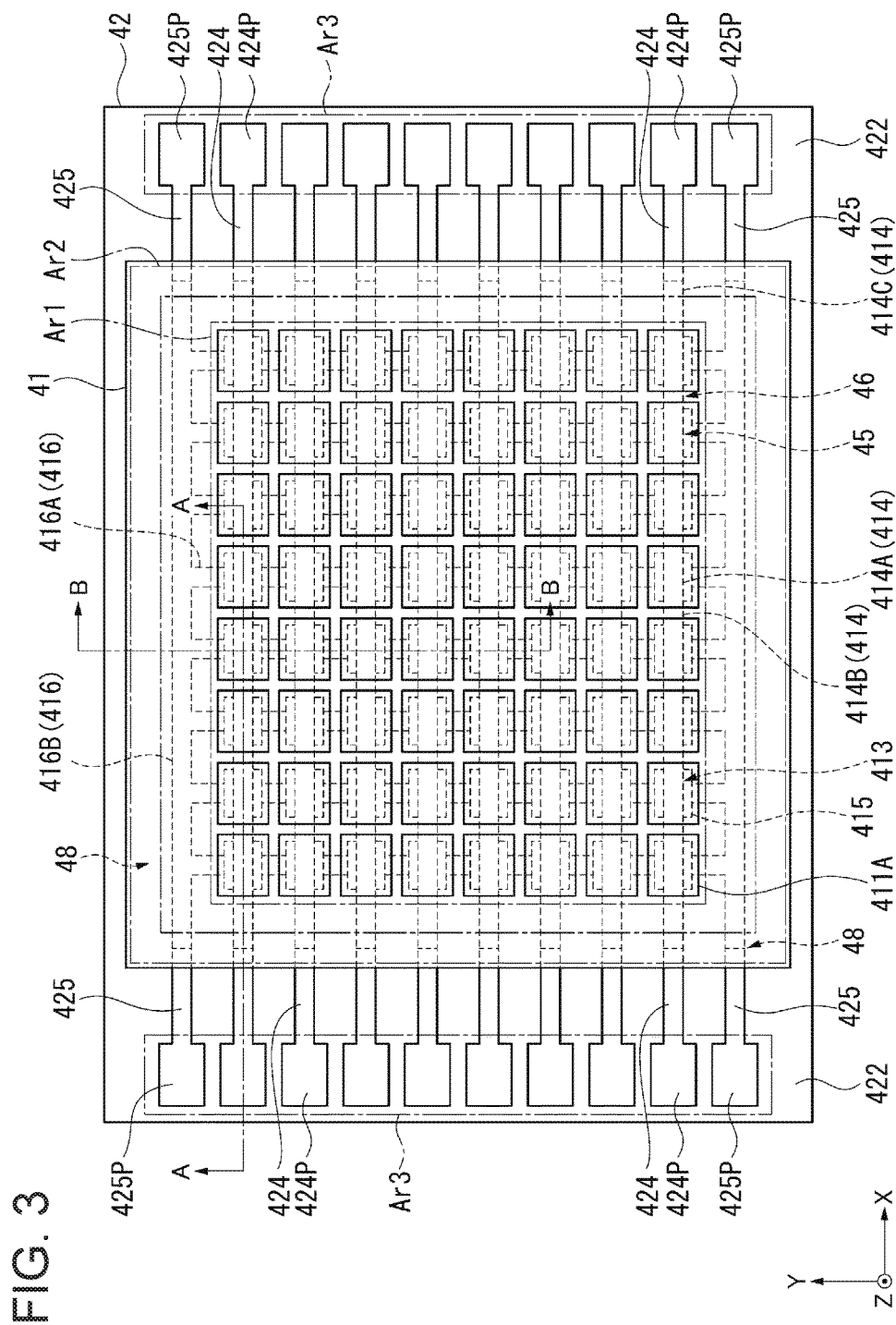
FIG. 3 is a plan view when an element substrate and a reinforcing plate in an ultrasonic device are viewed from the acoustic lens side.
Figure 4:
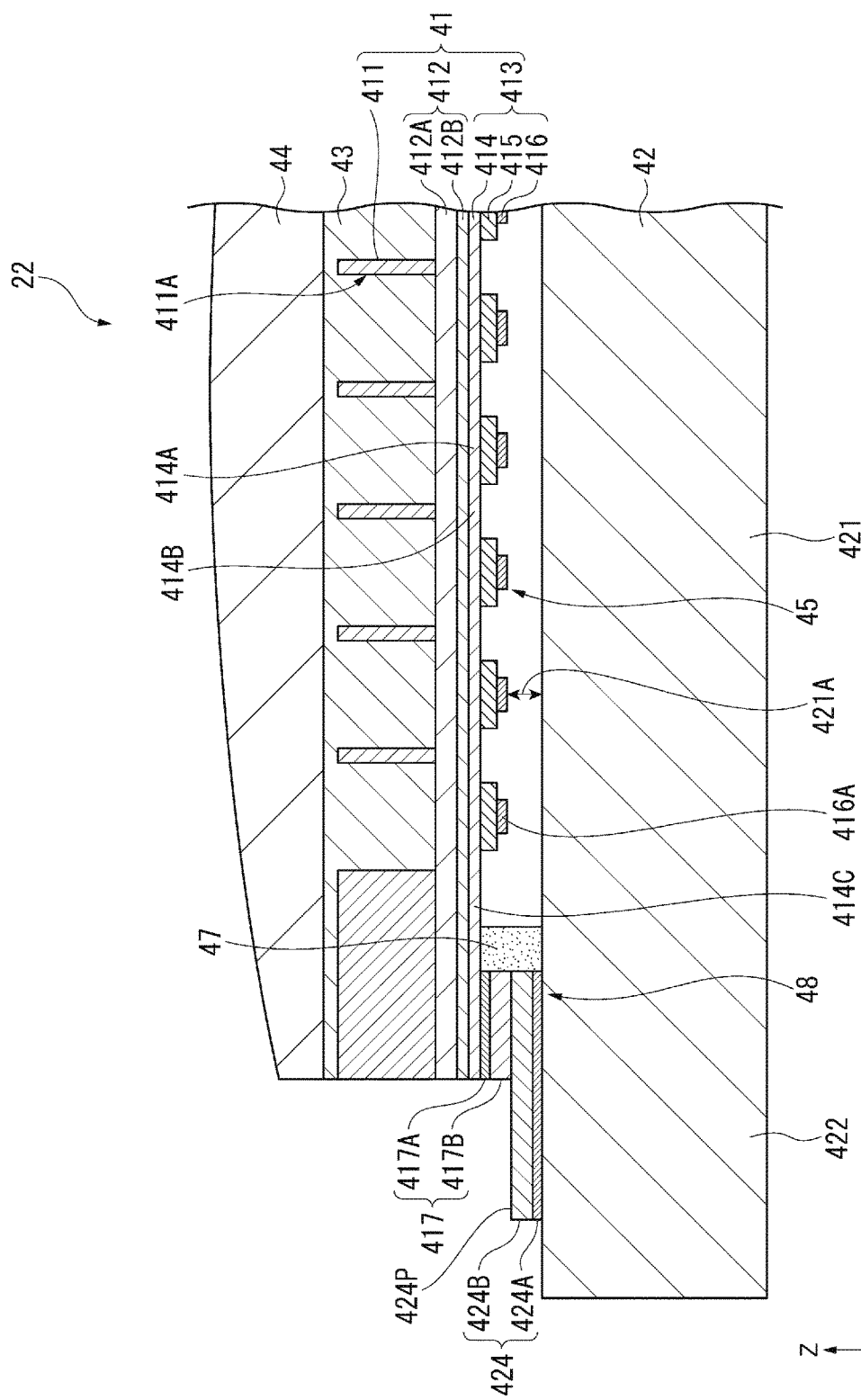
FIG. 4 is a sectional view of the ultrasonic device corresponding to line A-A in FIG. 3.
Figure 5:
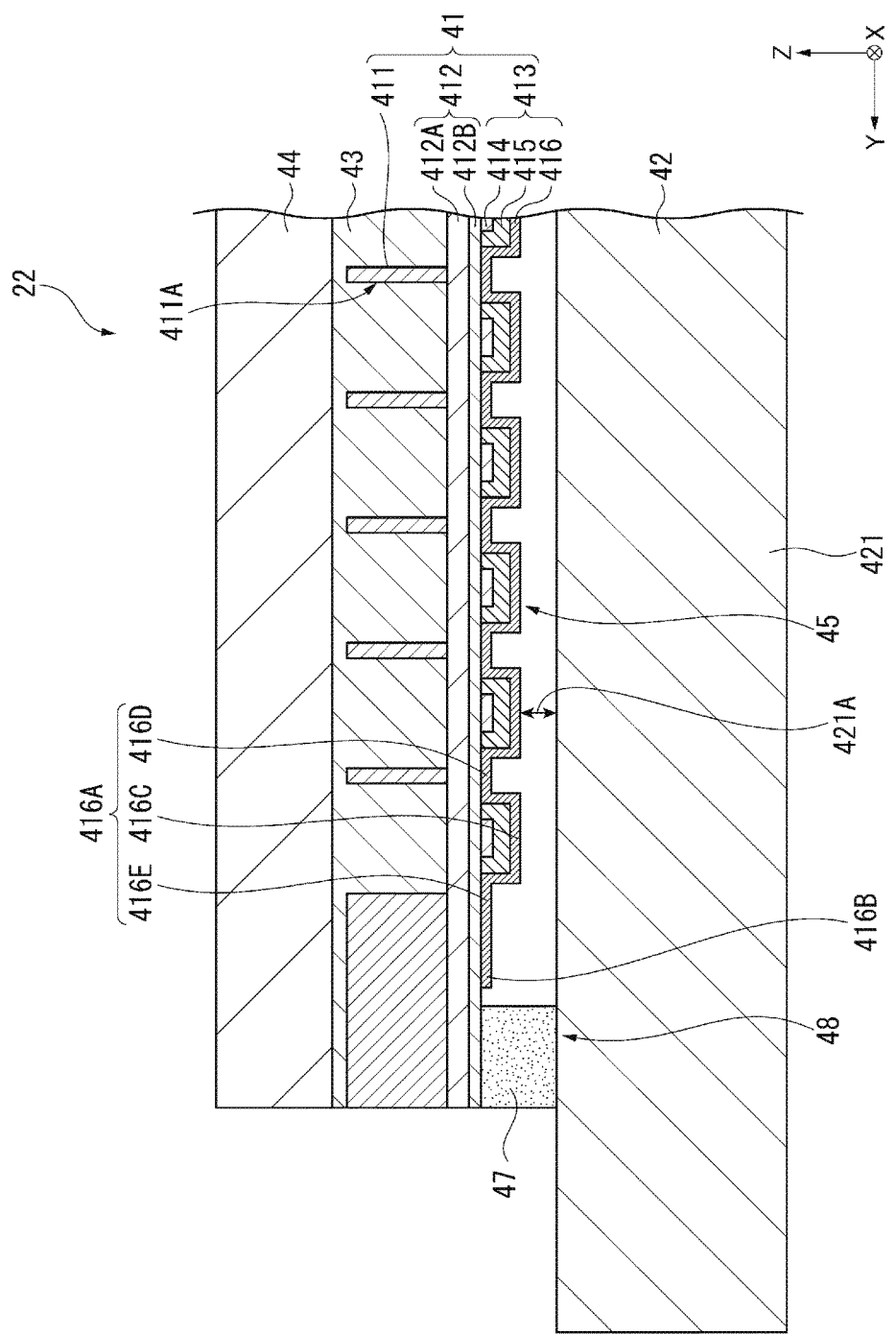
FIG. 5 is a sectional view of the ultrasonic device corresponding to line B-B in FIG. 3.
Figure 6:
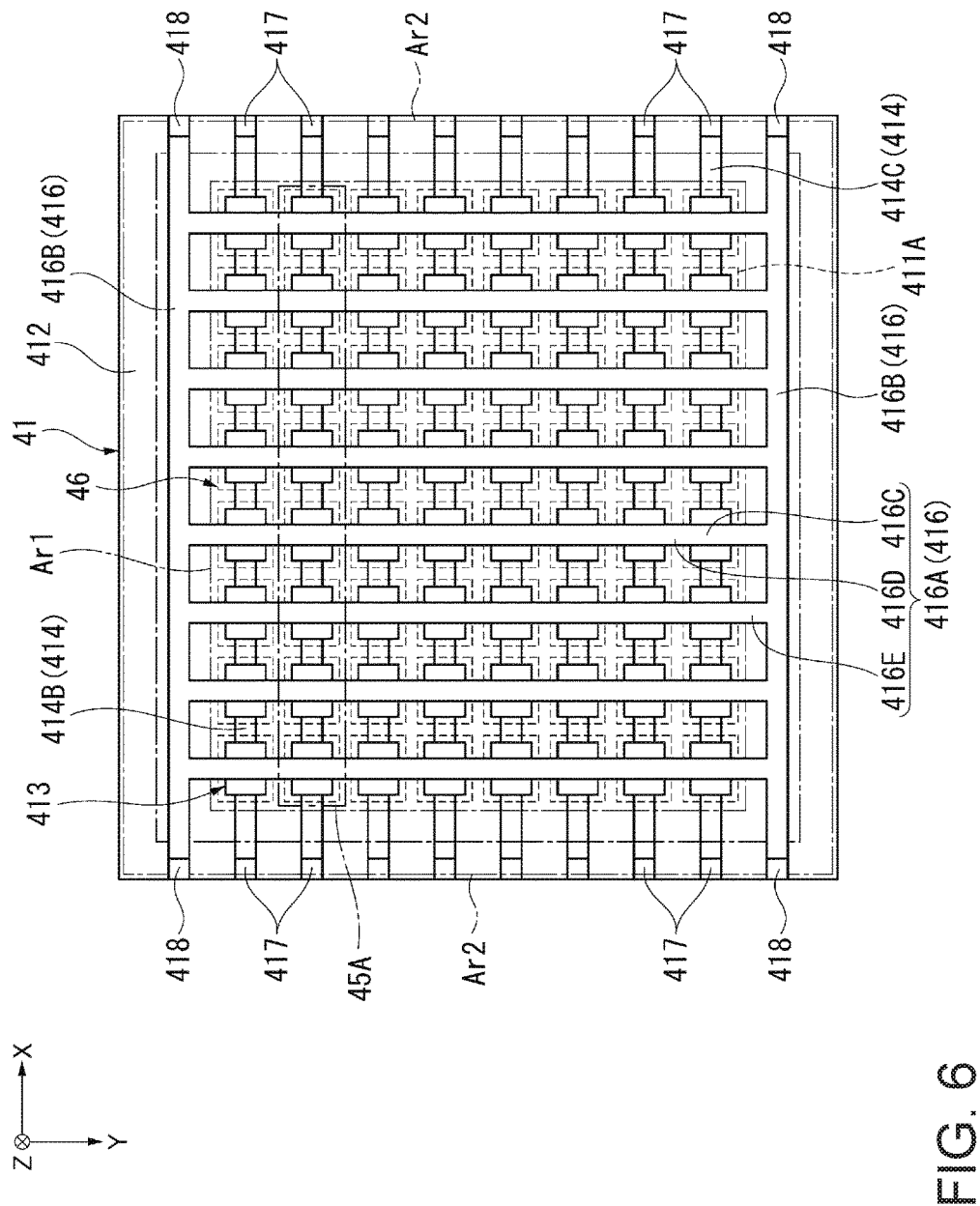
FIG. 6 is a plan view when the element substrate forming the ultrasonic device is viewed from the reinforcing plate side.
Figure 7:
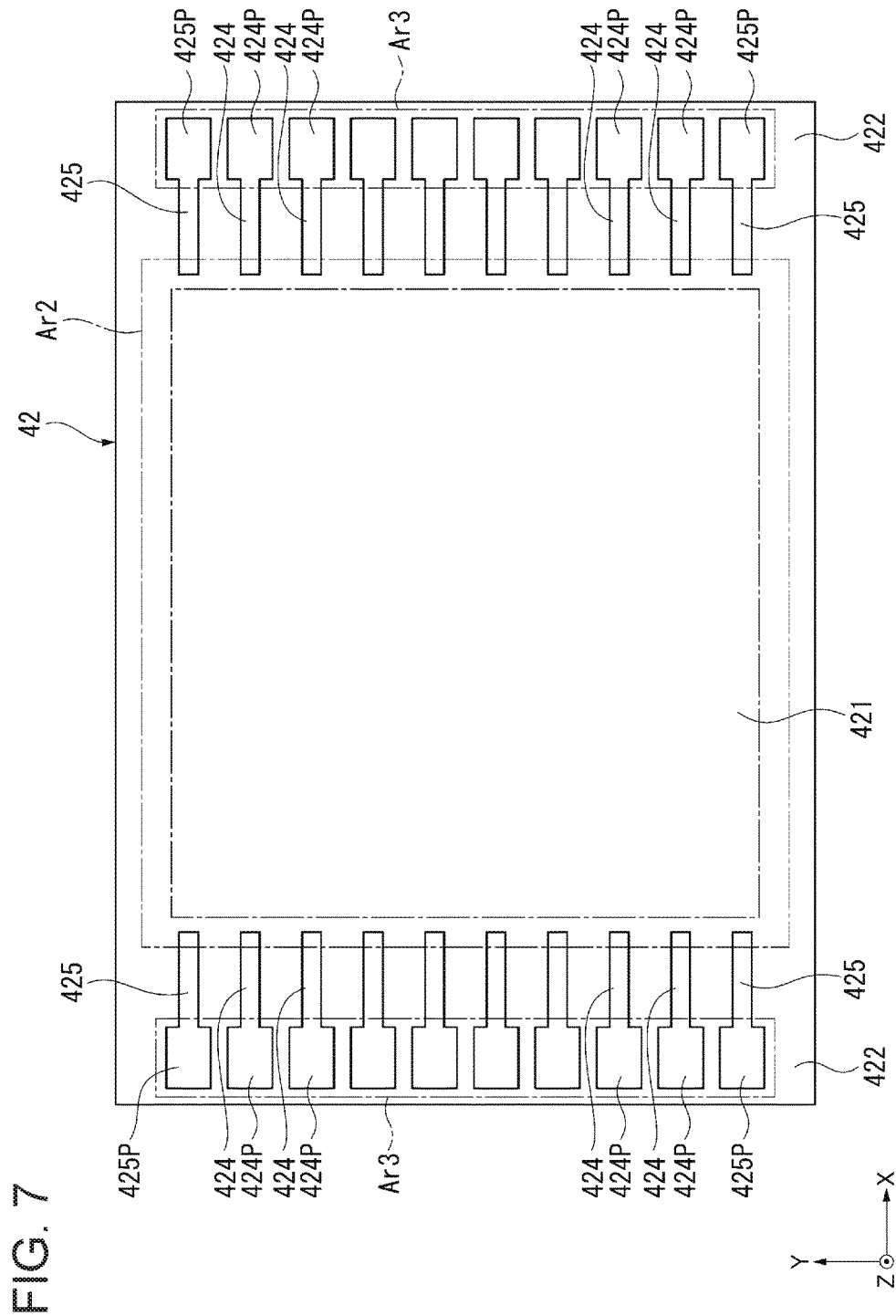
FIG. 7 is a plan view when the reinforcing plate forming the ultrasonic device is viewed from the element substrate side.

FIG. 3 is a plan view when an element substrate 41 and a reinforcing plate 42 in the ultrasonic device 22 are viewed from the acoustic lens 44 side. FIG. 4 is a sectional view of the ultrasonic device 22 corresponding to line A-A in FIG. 3. FIG. 5 is a sectional view of the ultrasonic device 22 corresponding to line B-B line in FIG. 3. FIG. 6 is a plan view when the element substrate 41 is viewed from the reinforcing plate 42 side. FIG. 7 is a plan view when the reinforcing plate 42 is viewed from the element substrate 41 side.

As shown in FIGS. 4 and 5, the ultrasonic device 22 includes the element substrate 41, the reinforcing plate 42, an acoustic matching layer 43, the acoustic lens 44, and a bonding member 47.

Configuration of Element Substrate

As shown in FIGS. 3 to 5, the element substrate 41 includes a substrate body portion 411, a vibration film 412 provided on the reinforcing plate 42 side of the substrate body portion 411, and a piezoelectric element 413 laminated on the vibration film 412. In addition, in a plan view when the element substrate 41 is viewed from the substrate thickness direction, the central region of the element substrate 41 is an array region Ar1, and a plurality of piezoelectric elements 413 are arranged in a matrix in the array region Ar1. The element substrate 41 is bonded to the reinforcing plate 42 by the bonding member 47 in a bonding region Ar2 that is located in the outer peripheral portion of the element substrate 41 in the above-described plan view.

The substrate body portion 411 is, for example, a semiconductor substrate formed of Si. In the array region Ar1 in the substrate body portion 411, an opening 411A corresponding to each piezoelectric element 413 is provided. Each opening 411A is closed by the vibration film 412 provided on the reinforcing plate 42 side of the substrate body portion 411.

The vibration film 412 is provided so as to cover the entire reinforcing plate 42 side of the substrate body portion 411. The thickness of the vibration film 412 is sufficiently smaller than the thickness of the substrate body portion 411.

In the present embodiment, as shown in FIGS. 4 and 5, the vibration film 412 includes a support layer 412A and a base layer 412B.

The support layer 412A is formed of, for example, $SiO_2$, is located on the substrate body portion 411 side, and closes the opening 411A. In a case where the substrate body portion 411 is formed of Si and the support layer 412A is formed of $SiO_2$, it is possible to easily form the support layer 412A by performing thermal oxidation treatment on the one substrate body portion 411.

The base layer 412B is formed of, for example, transition metal oxide such as $ZrO_2$, and is provided on a side of the support layer 412A opposite to the substrate body portion 411. The base layer 412B is located on the side of the support layer 412A opposite to the substrate body portion 411. The base layer 412B is a layer on which the piezoelectric element 413 is laminated.

In addition, the piezoelectric element 413 that is a laminate of a lower electrode 414, a piezoelectric film 415, and an upper electrode 416 is provided on the vibration film 412 (−Z side) that closes the opening 411A. By the vibration film 412 that closes the opening 411A and the piezoelectric element 413, one ultrasonic transducer 45 is formed.

In such an ultrasonic transducer 45, a rectangular wave voltage having a predetermined frequency can be applied between the lower electrode 414 and the upper electrode 416 to vibrate the vibration film 412 in the opening region of the opening 411A. As a result, it is possible to transmit ultrasonic waves. In addition, when the vibration film 412 is vibrated by ultrasonic waves reflected from the object, a potential difference occurs between the upper and lower sides of the piezoelectric film 415. Accordingly, it is possible to detect the received ultrasonic waves by detecting the potential difference between the lower electrode 414 and the upper electrode 416.

In the present embodiment, as shown in FIG. 6, a plurality of ultrasonic transducers 45 described above are arranged along an X direction (slice direction) and a Y direction (scanning direction) crossing the X direction (in the present embodiment, perpendicular to the X direction) in the predetermined array region Ar1 of the element substrate 41, thereby forming an ultrasonic transducer array 46.

Typically, a composite oxide having a lead zirconate titanate (PZT) based perovskite structure ($ABO_3$-type structure) can be used as the piezoelectric film 415. According to this, it becomes easy to ensure the amount of displacement of the piezoelectric element 413.

In addition, a composite oxide having a perovskite structure ($ABO_3$-type structure) containing no lead can be used as the piezoelectric film 415. According to this, the ultrasonic device 22 can be realized using a non-lead-based material having a less influence on the environment.

As such a non-lead-based piezoelectric material, for example, a BFO-based material containing bismuth ferrite (BFO; $BiFeO_3$) can be mentioned. In BFO, Bi is located at A site, and iron (Fe) is located at the B site. Other elements may be added to BFO. For example, at least one element selected from ferrate manganese (Mn), aluminum (Al), lanthanum (La), barium (Ba), titanium (Ti), cobalt (Co), cerium (Ce), samarium (Sm), chromium (Cr), potassium (K), lithium (Li), calcium (Ca), strontium (Sr), vanadium (V), niobium (Nb), tantalum (Ta), molybdenum (Mo), tungsten (W), nickel (Ni), zinc (Zn), praseodymium (Pr), neodymium (Nd), and Yuurobiumu (Eu) may be added to sodium potassium niobate (KNN; $KNaNbO_3$).

In addition, as another example of the non-lead-based piezoelectric material, a KNN-based material containing sodium potassium niobate (KNN) can be mentioned. Other elements may be added to KNN. For example, at least one element selected from manganese (Mn), lithium (Li), barium (Ba), calcium (Ca), strontium (Sr), zirconium (Zr), titanium (Ti), bismuth (Bi), tantalum (Ta), antimony (Sb), iron (Fe), cobalt (Co), silver (Ag), magnesium (Mg), zinc (Zn), copper (Cu), vanadium (V), chromium (Cr), molybdenum (Mo), tungsten (W), nickel (Ni), aluminum (Al), silicon (Si), lanthanum (La), cerium (Ce), praseodymium (Pr), neodymium (Nd), promethium (Pm), samarium (Sm), and europium (Eu) may be added to KNN.

Materials of the lower electrode 414 or the upper electrode 416 are not limited as long as the materials are conductive materials. As examples of the material of the lower electrode 414 or the upper electrode 416, it is possible to use metal materials such as platinum (Pt), iridium (Ir), gold (Au), aluminum (Al), copper (Cu), titanium (Ti), and stainless steel, tin oxide based conductive materials such as indium tin oxide (ITO) and fluorine doped tin oxide (FTC), zinc oxide based conductive materials, oxide conductive materials such as ruthenium acid strontium ($SrRuO_3$), nickel lanthanum ($LaNiO_3$), and earth doped strontium titanate, and a conductive polymer.

As shown in FIG. 6, the lower electrode 414 is formed in a linear shape along the X direction. That is, the lower electrode 414 is provided over a plurality of ultrasonic transducers 45 aligned along the X direction, and is formed by a lower electrode body 414A located between the piezoelectric film 415 and the vibration film 412, a lower connection electrode 414B that connects the adjacent lower electrode bodies 414A to each other, and a lower lead electrode 414C drawn to the bonding region Ar2 outside the array region Ar1 (refer to FIG. 4). Accordingly, in the ultrasonic transducers 45 aligned in the X direction, the lower electrode 414 has the same electric potential.

The lower lead electrode 414C extends to the bonding region Ar2 from the array region Ar1.

As shown in FIGS. 3 and 4, each of the plurality of lower electrodes 414 is electrically connected to a second lower connection electrode 424 provided on the reinforcing plate 42 side by being in contact with the second lower connection electrode 424 through a first lower connection electrode 417 provided on the lower lead electrode 414C (−Z side) in the bonding region Ar2. As will be described later, each lower electrode 414 is connected to the circuit board 23 through a lower electrode pad 424P of the second lower connection electrode 424.

The first lower connection electrode 417 has a first layer 417A located on the element substrate 41 side and a second layer 417B provided on the first layer 417A. The first layer 417A is formed of, for example, a metal material, such as NiCr alloy. The second layer 424B is formed of, for example, a metal material, such as Au.

The configuration of the first lower connection electrode 417 is not limited to the configuration described above, and may be formed of a metal material of one layer or three or more layers. In addition to the metal material described above, various conductive materials can be used as materials forming the first lower connection electrode 417, similar to the lower electrode 414 and the upper electrode 416.

On the other hand, as shown in FIG. 6, the upper electrode 416 includes an element electrode portion 416A, which is provided over a plurality of ultrasonic transducers 45 aligned along the Y direction, and a common electrode portion 416B that connects the ends of the plurality of element electrode portions 416A to each other. The element electrode portion 416A has an upper electrode body 416C laminated on the piezoelectric film 415, an upper connection electrode 416D that connects the adjacent upper electrode bodies 416C to each other, and an upper lead electrode 416E that extends to the outside along the Y direction from the ultrasonic transducers 45 disposed at both ends in the Y direction (refer to FIG. 5).

The common electrode portion 416B is provided in each of the +Y-side end and the −Y-side end of the array region Ar1. The common electrode portion 416B on the +Y side connects the upper lead electrodes 416E extending to the +Y side from the ultrasonic transducer 45 provided on the +Y side end, among a plurality of ultrasonic transducers 45 provided along the Y direction. The common electrode portion 416B at the −Y side end connects the upper lead electrodes 416E extending to the −Y side. Accordingly, in each ultrasonic transducer 45 within the array region Ar1, the upper electrode 416 has the same electric potential. The pair of upper lead electrodes 416E are provided along the X direction, and the ends thereof extends to the bonding region Ar2 from the array region Ar1.

As shown in FIGS. 3 and 5, each of the pair of upper lead electrodes 416E is electrically connected to a second upper connection electrode 425 provided on the reinforcing plate 42 side by being in contact with the second upper connection electrode 425 through a first upper connection electrode 418 provided on the upper lead electrode 416E (−Z side) in the bonding region Ar2. As will be described later, a pair of upper lead electrodes 416E are connected to the circuit board 23 through an upper electrode pad 425P of the second upper connection electrode 425.

Although not shown, the first upper connection electrode 418 has a first layer located on the element substrate 41 side and a second layer located on the first layer (−Z side), similar to the first lower connection electrode 417. The first upper connection electrode 418 may be formed of a metal material of one layer or three or more layers. In addition to the metal material described above, various conductive materials can be used as materials forming the first upper connection electrode 418, similar to the lower electrode 414 and the upper electrode 416.

In the ultrasonic transducer array 46 described above, one ultrasonic transducer group 45A is formed by the ultrasonic transducers 45 aligned in the X direction, which are connected to each other by the lower electrode 414, and a plurality of ultrasonic transducer groups 45A are aligned along the Y direction to form a one-dimensional array structure.

Configuration of Reinforcing Plate

The reinforcing plate 42 is a plate-shaped member, such as a semiconductor substrate formed of Si or an insulator substrate, for example. As shown in FIG. 3, the reinforcing plate 42 has an opposite portion 421 facing the element substrate 41 and a protruding portion 422, which extends in +X and −X directions from the opposite portion 421 and protrudes to the element substrate 41 in a plan view as viewed from the thickness direction, and has a larger outer size than the element substrate 41.

In addition, since the material or shape of the reinforcing plate 42 affects the frequency characteristics of the ultrasonic transducer 45, it is preferable to set the material or shape of the reinforcing plate 42 based on the center frequency of ultrasonic waves transmitted and received by the ultrasonic transducer 45.

When the vibration film 412 is vibrated, ultrasonic waves are emitted as back waves not only to the opening 411A side but also to the reinforcing plate 42 side. The back wave is reflected by the reinforcing plate 42, and is emitted to the vibration film 412 side again through a gap 421A. In this case, if the phase of the reflected back wave and the phase of the ultrasonic wave emitted to the opening 411A side from the vibration film 412 are shifted from each other, the ultrasonic wave is attenuated. In the present embodiment, therefore, an acoustic distance in the gap 421A is set to be an odd multiple of ¼ ($\lambda/4$) of the wavelength $\lambda$ of the ultrasonic wave.

In addition, as shown in FIG. 7, the second lower connection electrode 424 and the second upper connection electrode 425 are provided on the surface of the reinforcing plate 42 facing the element substrate 41.

The second lower connection electrode 424 is provided for each of a plurality of first lower connection electrodes 417 formed on the element substrate 41, and is electrically connected to the corresponding first lower connection electrode 417 by being in contact with the corresponding first lower connection electrode 417 in the bonding region Ar2 facing the outer peripheral portion of the element substrate 41. The second lower connection electrode 424 extends to a terminal region Ar3 of the protruding portion 422 from the bonding region Ar2, thereby forming the lower electrode pad 424P in the terminal region Ar3. The lower electrode pad 424P is connected to a terminal portion 231 provided on the circuit board 23 by a wiring member (not shown), such as a flexible printed circuit (FPC).

The second lower connection electrode 424 has a first layer 424A formed on the reinforcing plate 42 and a second layer 424B formed on the first layer 424A (+Z side). The first layer 424A is formed of, for example, a metal material, such as NiCr alloy. The second layer 424B is formed of, for example, a metal material, such as Au. The configuration of the second lower connection electrode 424 is not limited to the configuration described above, and may be formed of a metal material of one layer or three or more layers. In addition to the metal material described above, various conductive materials can be used as materials forming the second lower connection electrode 424, similar to the lower electrode 414 and the upper electrode 416.

The second upper connection electrode 425 is provided for each of a plurality of first upper connection electrodes 418 formed on the element substrate 41, and is electrically connected to the corresponding first upper connection electrode 418 by being in contact with the corresponding first upper connection electrode 418 in the bonding region Ar2. The second upper connection electrode 425 extends to the terminal region Ar3 of the protruding portion from the bonding region Ar2, thereby forming the upper electrode pad 425P in the terminal region Ar3. The upper electrode pad 425P is connected to the terminal portion 231 provided on the circuit board 23 by the above-described wiring member (not shown).

Although not shown, the second upper connection electrode 425 has a first layer disposed on the reinforcing plate 42 (+Z side) and a second layer formed on the first layer, similar to the second lower connection electrode 424. The second upper connection electrode 425 may be formed of a metal material of one layer or three or more layers. In addition to the metal material described above, various conductive materials can be used as materials forming the first lower connection electrode 417, similar to the lower electrode 414 and the upper electrode 416.

Configuration of Bonding Member

As shown in FIG. 3, the bonding member 47 is disposed in at least a part of a bonding portion 48 provided in the bonding region Ar2 between the element substrate 41 and the reinforcing plate 42 in a plan view as viewed from the thickness direction of the element substrate 41, and bonds the element substrate 41 and the reinforcing plate 42 to each other. That is, the bonding portion 48 is configured to include at least either parts of the first lower connection electrode 417, the first upper connection electrode 418, the second lower connection electrode 424, and the second upper connection electrode 425 or the bonding member 47 (refer to FIGS. 3 and 4 and the like). In the bonding portion 48, the element substrate 41 and the reinforcing plate 42 are bonded to each other, and the first lower connection electrode 417 and the second lower connection electrode 424 are connected to each other and the first upper connection electrode 418 and the second upper connection electrode 425 are connected to each other.

In the bonding region Ar2, the bonding member 47 is disposed so as to surround the array region Ar1. Accordingly, a region (including the array region Ar1) where the element substrate 41 and the reinforcing plate 42 face each other is sealed by being surrounded by the bonding member 47. As the bonding member 47, it is possible to use various adhesives. However, permeation of water into the array region Ar1 can be appropriately suppressed, for example, by using an epoxy based adhesive. Therefore, it is possible to suppress the deterioration of the piezoelectric element 413.

Configuration of Acoustic Matching Layer and Acoustic Lens

As shown in FIGS. 4 and 5, the acoustic matching layer 43 is provided on the opening 411A side of the element substrate 41. Specifically, the acoustic matching layer 43 is filled in the opening 411A of the element substrate 41, and is formed in a predetermined thickness from the +Z side end surface of the substrate body portion 411.

The acoustic lens 44 is provided on the acoustic matching layer 43, and is exposed to the outside from the sensor window 21B of the housing 21 as shown in FIG. 1.

Due to the acoustic matching layer 43 or the acoustic lens 44, ultrasonic waves transmitted from the ultrasonic transducer 45 efficiently propagate toward the living body that is a measurement target, and ultrasonic waves reflected from the inside of the living body efficiently propagate toward the ultrasonic transducer 45. For this reason, the acoustic impedance of the acoustic matching layer 43 and the acoustic lens 44 is set to the intermediate acoustic impedance between the acoustic impedance of the ultrasonic transducer 45 of the element substrate 41 and the acoustic impedance of the living body.

Configuration of Circuit Board

As shown in FIG. 2, the circuit board 23 has the terminal portion 231 connected to the lower electrode pad 424P or the upper electrode pad 425P provided on the element substrate 41. In addition, a driver circuit for driving the ultrasonic device 22 or the like is provided on the circuit board 23. Specifically, as shown in FIG. 2, the circuit board 23 includes a selection circuit 232, a transmission circuit 233, a receiving circuit 234, and the like.

The selection circuit 232 switches a transmission connection for connecting the ultrasonic device 22 and the transmission circuit 233 and a reception connection for connecting the ultrasonic device 22 and the receiving circuit 234 based on the control of the control device 10.

When switching to the transmission connection is made by the control of the control device 10, the transmission circuit 233 outputs a signal, which indicates the transmission of ultrasonic waves, to the ultrasonic device 22 through the selection circuit 232.

When switching to the reception connection is made by the control of the control device 10, the receiving circuit 234 outputs a detection signal, which is input from the ultrasonic device 22 through the selection circuit 232, to the control device 10. The receiving circuit 234 is configured to include, for example, a low noise amplifier circuit, a voltage controlled attenuator, a programmable gain amplifier, a low pass filter, and an A/D converter. The receiving circuit 234 performs various kinds of signal processing, such as the conversion of a received signal to a digital signal, removal of noise components, and amplification to a desired signal level, and then outputs the received signal after the processing to the control device 10.

Configuration of Control Device

As shown in FIG. 2, the control device 10 is configured to include, for example, an operating unit 11, a display unit 12, a storage unit 13, and a calculation unit 14. As examples of the control device 10, a terminal device, such as a tablet terminal, a smartphone, or a personal computer, may be used, or a dedicated terminal device for operating the ultrasonic probe 2 may be used.

The operating unit 11 is a user interface (UI) used when the user operates the ultrasonic measurement apparatus 1. For example, the operating unit 11 can be configured to include a touch panel provided on the display unit 12, operation buttons, a keyboard, a mouse, or the like.

The display unit 12 is formed using, for example, a liquid crystal display, and displays an image thereon.

The storage unit 13 stores various programs and various kinds of data for controlling the ultrasonic measurement apparatus 1.

The calculation unit 14 is configured to include, for example, an arithmetic circuit, such as a central processing unit (CPU), and a storage circuit, such as a memory. The calculation unit 14 reads various programs stored in the storage unit 13 and executes the various programs, thereby performing the generation of a transmission signal and the control of output processing for the transmission circuit 233 and performing received signal frequency setting, gain setting, or the like for the receiving circuit 234.

Ultrasonic Device Manufacturing Method

Next, a method of manufacturing the above ultrasonic device 22 will be described.

Figure 8:
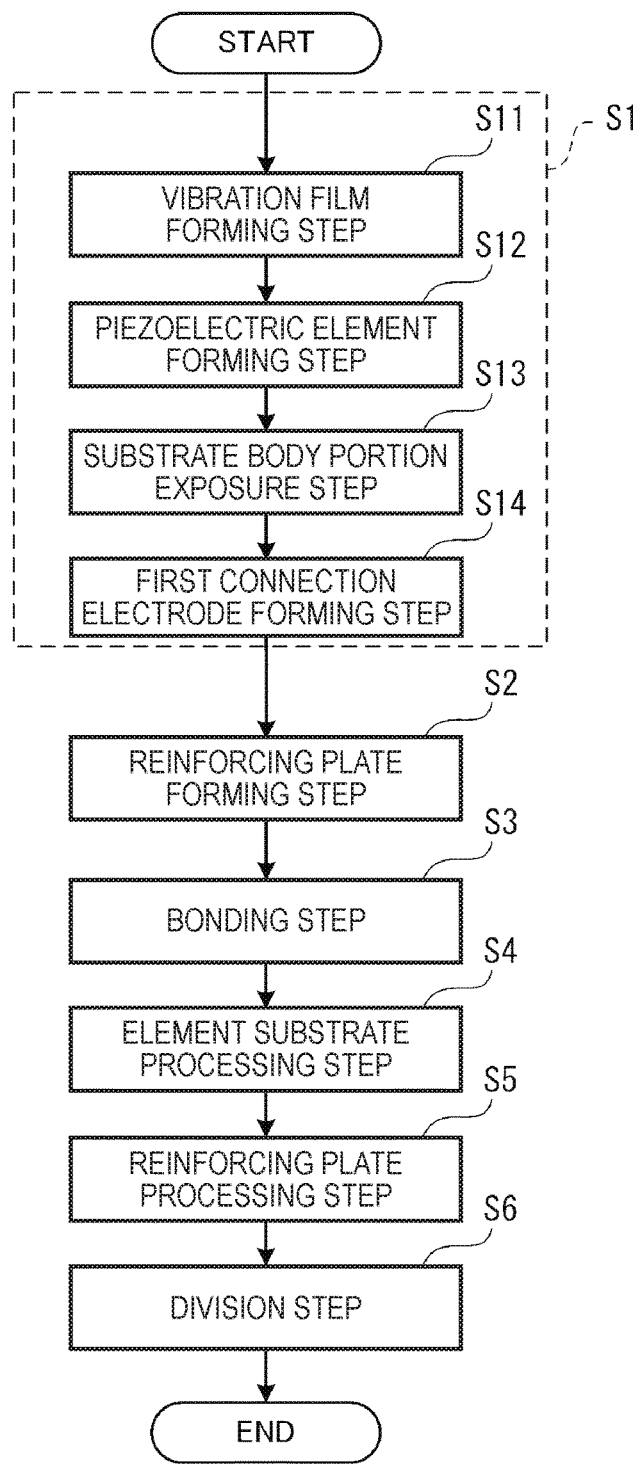
FIG. 8 is a flowchart showing a method of manufacturing an ultrasonic device.

FIG. 8 is a flowchart showing each step in the manufacturing of the ultrasonic device 22 of the present embodiment. FIGS. 9 to 22 are diagrams showing the outline of the ultrasonic device 22 in each step.

In order to manufacture the ultrasonic device 22, as shown in FIG. 8, an element substrate forming step S1, a reinforcing plate forming step S2, a bonding step S3, an element substrate processing step S4, a reinforcing plate processing step S5, and a division step S6 are performed. That is, in the present embodiment, a plurality of element substrates 41 are integrally formed for an Si substrate and a plurality of reinforcing plates 42 are integrally formed in the same manner, and these are bonded to each other. Then, each of the element substrates 41 that are integrally formed is divided in the element substrate processing step S4 and then the reinforcing plate 42 is divided in the division step S6, thereby forming a plurality of ultrasonic devices 22.

FIGS. 9 to 22 show cross sections taken along the line A-A shown in FIG. 3. In addition, a virtual line L2 shown in FIGS. 14 to 22 shows a division position when dividing the reinforcing plate 42 in the division step S6.

Element Substrate Forming Step

Figure 9:
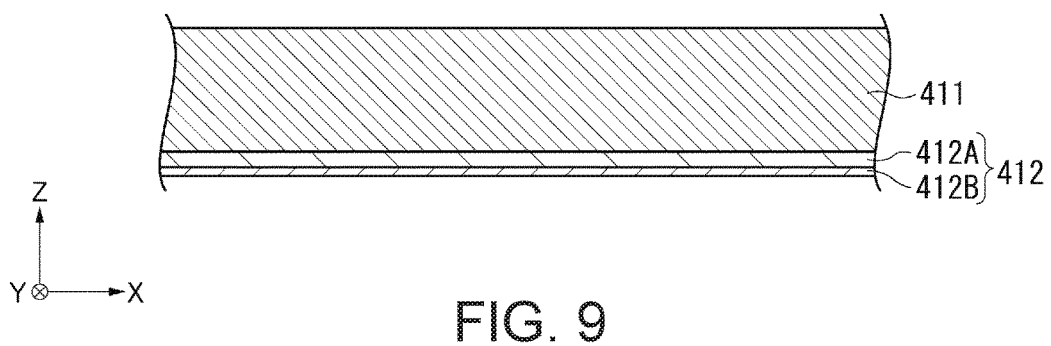
FIG. 9 is a diagram showing the state of an ultrasonic device in an element substrate forming step.
Figure 10:
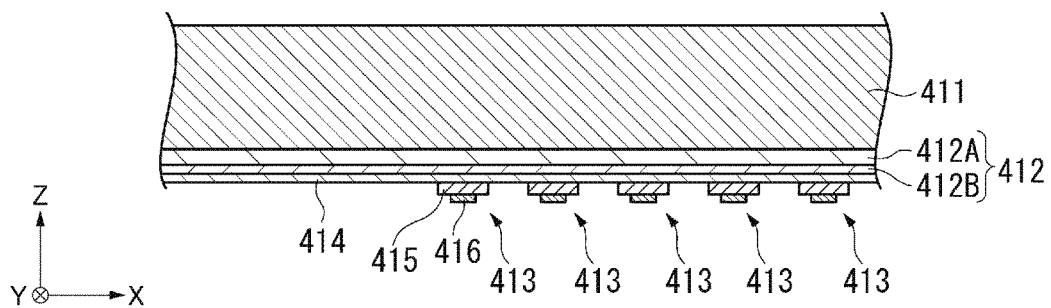
FIG. 10 is a diagram showing the state of the ultrasonic device in the element substrate forming step.

In the element substrate forming step S1, first, the vibration film 412 is formed in the substrate body portion 411 formed of Si (step S11: vibration film forming step). In step S11, an $SiO_2$ film that is the support layer 412A is formed by performing thermal oxidation treatment on the substrate body portion 411. In addition, a $ZrO_2$ layer that is the base layer 412B is formed by forming Zr on the $SiO_2$ film and performing thermal oxidation treatment. Therefore, as shown in FIG. 9, the vibration film 412 is formed on the substrate body portion 411.

Then, the piezoelectric element 413 is formed by forming the lower electrode 414, the piezoelectric film 415, and the upper electrode 416 on the vibration film 412 (step S12: piezoelectric element forming step). In step S12, first, an electrode material forming the lower electrode 414 is formed on the vibration film 412 by sputtering, for example. Then, a resist is applied on the lower electrode 414, a resist pattern is formed by photolithography or the like, and the lower electrode 414 is patterned by etching, for example. As the lower electrode 414, for example, a layer of Ti, Ir, and Pt having a total thickness of about 200 nm is formed.

Then, the piezoelectric film 415 is formed on the lower electrode 414. The piezoelectric film 415 is formed by a solution method using PZT, for example. For example, application processing for applying the PZT solution with a composition ratio of Zr:Ti=52:48 on the vibration film 412 and the lower electrode 414 and baking processing for baking the applied PZT solution under the conditions of, for example, pre-baking of 400° C. and RTA baking of 700° C. are performed multiple times, thereby obtaining a piezoelectric layer having a desired thickness. Then, the piezoelectric film 415 is formed by patterning the formed piezoelectric layer by etching (ion milling). The thickness of the piezoelectric film 415 is 1200 nm.

After forming the piezoelectric film 415, the upper electrode 416 is formed in the same manner as for the lower electrode 414. That is, an electrode material is formed on the vibration film 412, and a resist pattern is formed and patterned by etching or the like in the same manner as at the time of the lower electrode 414. As the upper electrode 416, for example, an Ir layer having a thickness of 50 nm is formed.

As described above, as shown in FIG. 10, the piezoelectric element 413 configured to include the lower electrode 414, the piezoelectric film 415, and the upper electrode 416 is formed on the vibration film 412.

Figure 11:
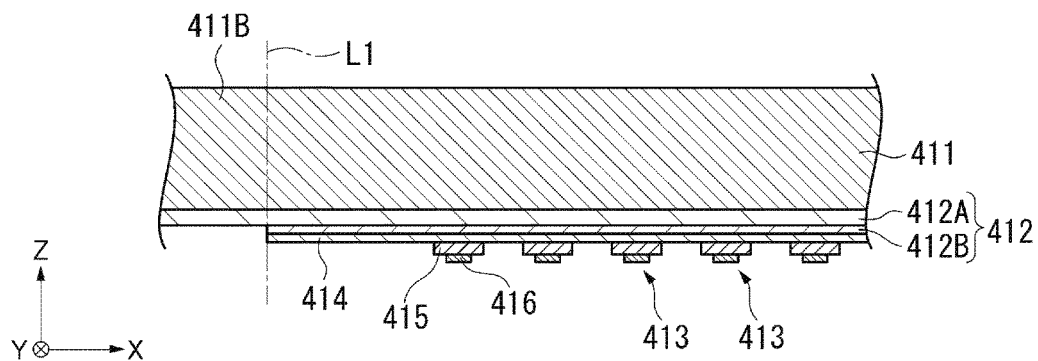
FIG. 11 is a diagram showing the state of the ultrasonic device in the element substrate forming step.
Figure 12:
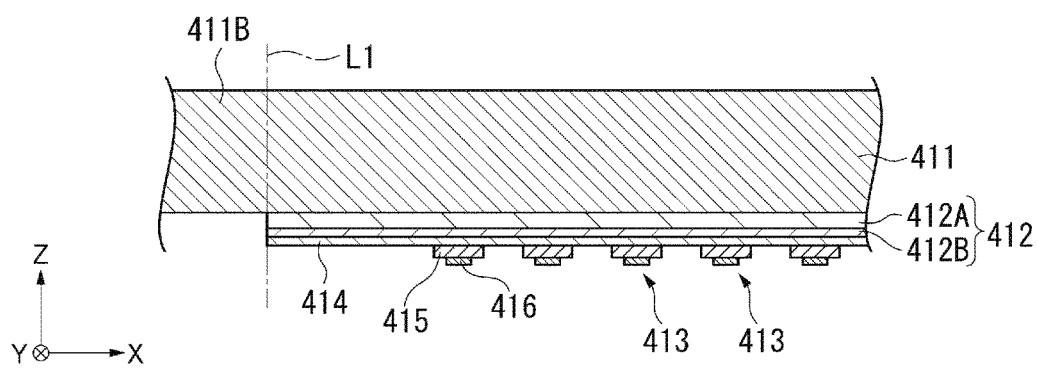
FIG. 12 is a diagram showing the state of the ultrasonic device in the element substrate forming step.

Then, as shown in FIG. 12, the vibration film 412 formed on the surface of a removal portion 411B, which is a portion to be removed when dividing the element substrate 41 in the element substrate processing step S4 is removed, in the substrate body portion 411, so that the substrate body portion 411 is exposed (step S13: substrate body portion exposure step). The removal portion 411B is a portion other than a portion corresponding to the element substrate 41 (portion located outside a portion corresponding to the element substrate 41) in a plan view as viewed from the thickness direction. After performing the bonding step S3, the removal portion 411B includes at least a region facing the second lower connection electrode 424 or the second upper connection electrode 425. In addition, a position indicated by a virtual line L1 (refer to FIG. 11 and the like) is a position corresponding to the outer edge of the element substrate 41. In the example shown in FIGS. 11 to 13, the removal portion 411B is a portion closer to the −X side than the virtual line L1 is.

In step S13, first, a mask is formed in a region of the −Z-side surface of the substrate body portion 411 excluding the removal portion 411B, the base layer 412B formed on the removal portion 411B is removed by etching, and then the mask is removed (refer to FIG. 11). Then, similarly, a mask is formed in a region other than the removal portion 411B, the support layer 412A formed on the removal portion 411B is removed by etching, and then the mask is removed (refer to FIG. 12). In this manner, the surface of the removal portion 411B in the substrate body portion 411 is exposed. That is, in a region of the substrate body portion 411 excluding the region corresponding to the element substrate 41, the surface of the substrate body portion 411 is exposed. The removal portion 411B is equivalent to an exposed portion that is exposed in step S13.

Figure 13:
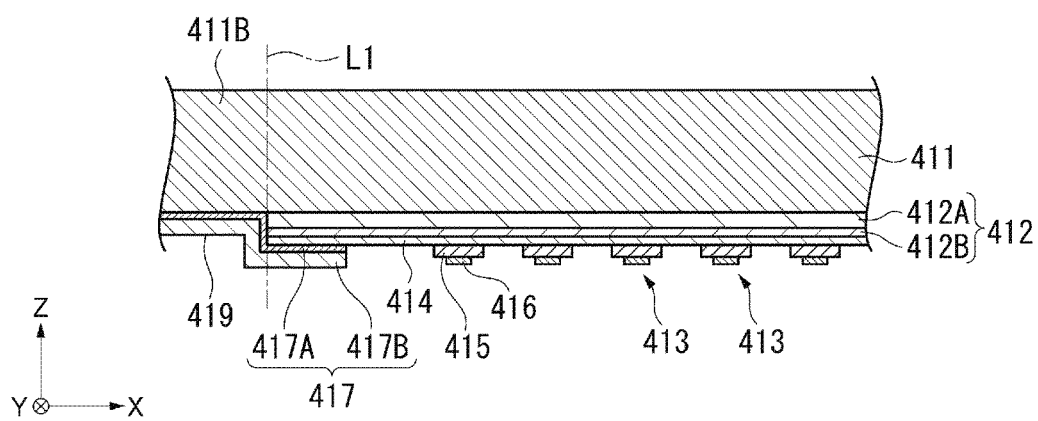
FIG. 13 is a diagram showing the state of the ultrasonic device in the element substrate forming step.
Figure 14:
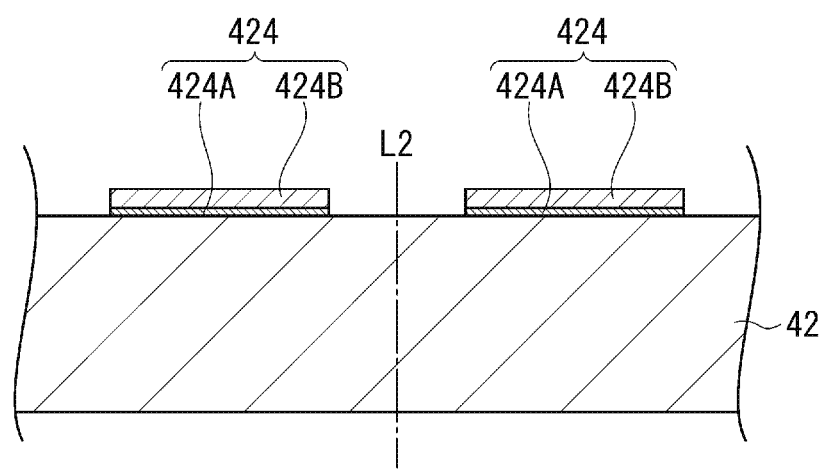
FIG. 14 is a diagram showing the state of the ultrasonic device in a reinforcing plate forming step.

Then, the first lower connection electrode 417 and the first upper connection electrode 418 are formed (step S14: first connection electrode forming step). In step S14, for example, an NiCr layer (corresponding to the first layers of the first lower connection electrode 417 and the first upper connection electrode 418) having a thickness of 50 nm and an Au layer (corresponding to the second layers of the first lower connection electrode 417 and the first upper connection electrode 418) having a thickness of 1300 nm are sequentially formed by sputtering or the like. Then, a mask is formed on the formation position of the first lower connection electrode 417 and the first upper connection electrode 418 and on the removal portion 411B, the NiCr layer and the Au layer other than the mask forming region are removed, and then the mask is removed. Therefore, as shown in FIG. 13, the first lower connection electrode 417 is formed on the formation position of the first lower connection electrode 417 and the removal portion 411B. In this case, the first upper connection electrode 418 (refer to FIG. 6) is also simultaneously formed.

In the following explanation, portions of the first lower connection electrode 417 and the first upper connection electrode 418 formed in step S14, which are formed on the removal portion 411B, are referred to as a metal layer 419. As described above, the vibration film 412 formed on the removal portion 411B is replaced with the metal layer 419 in steps S13 and S14. The metal layer 419 is formed in a region of the substrate body portion 411 excluding the region corresponding to the element substrate 41. In addition, although will be described in detail later, the metal layer 419 can function as an etching stopper layer when forming the substrate body portion 411 by wet etching in the element substrate processing step S4, so that the permeation of an etchant into the ultrasonic device 22 can be prevented.

Reinforcing Plate Forming Step

Figure 15:
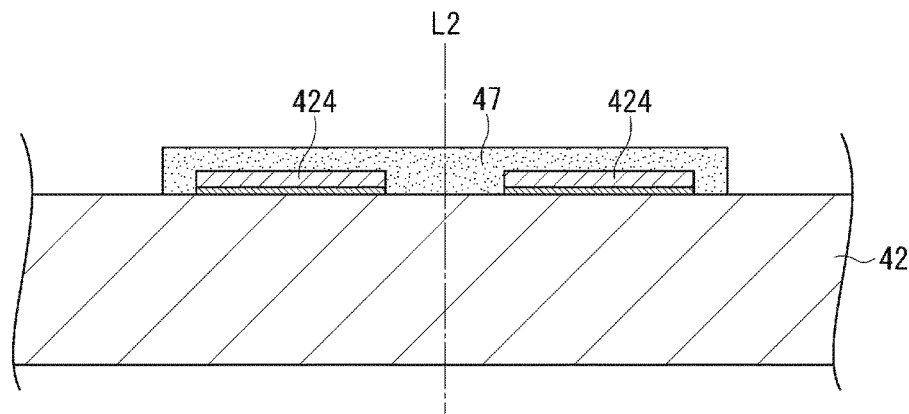
FIG. 15 is a diagram showing the state of the ultrasonic device in a bonding step.

Then, the reinforcing plate forming step S2 is performed. In the reinforcing plate forming step S2, the second lower connection electrode 424 and the second upper connection electrode 425 are formed. In step S2, for example, an NiCr layer (corresponding to the first layers of the second lower connection electrode 424 and the second upper connection electrode 425) having a thickness of 50 nm and an Au layer (corresponding to the second layers of the second lower connection electrode 424 and the second upper connection electrode 425) having a thickness of 1300 nm are sequentially formed by sputtering or the like. Then, a mask is formed on the formation position of the second lower connection electrode 424 and the second upper connection electrode 425, the NiCr layer and the Au layer other than the mask forming region are removed, and then the mask is removed. In this manner, as shown in FIG. 15, the second lower connection electrode 424 is formed. In this case, the second upper connection electrode 425 (refer to FIG. 7) is also simultaneously formed. In the case of forming the reinforcing plate 42 using an Si substrate, thermal oxidation treatment may be performed on the reinforcing plate 42 to form an oxide layer of $SiO_2$ on the surface of the reinforcing plate 42.

Bonding Step

Figure 16:
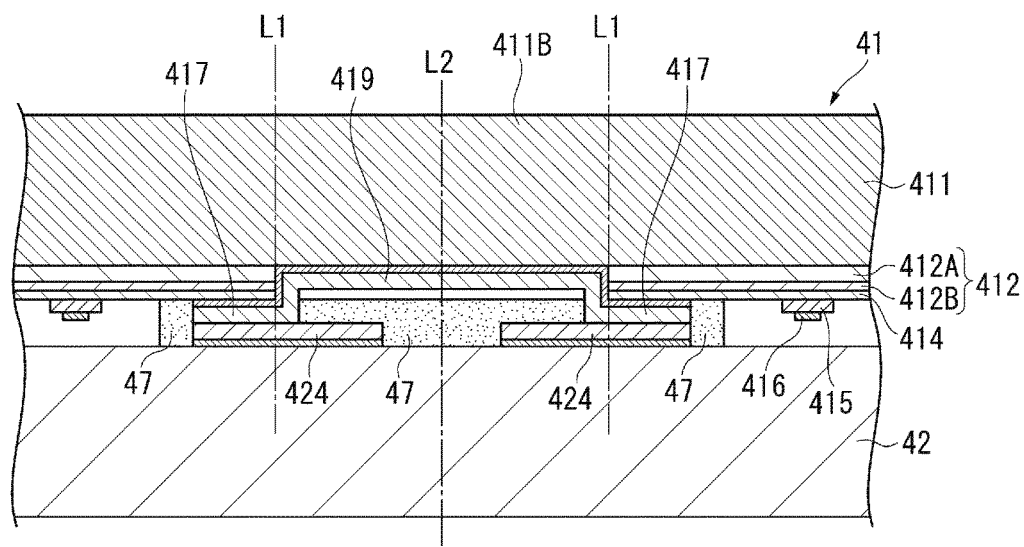
FIG. 16 is a diagram showing the state of the ultrasonic device in the bonding step.

Then, the bonding step S3 is performed. In the bonding step S3, as shown in FIG. 16, the bonding member 47 is disposed on the reinforcing plate 42. In the present embodiment, an epoxy based adhesive is used as the bonding member 47. The bonding member 47 is disposed in at least a position covering the second lower connection electrode 424 and the second upper connection electrode 425 and the bonding region Ar2 (refer to FIG. 7). Specifically, for example, the bonding member 47 is disposed on the reinforcing plate 42 by transferring the bonding member 47 from a film to the reinforcing plate 42 after applying the bonding member 47 on the film.

Figure 17:
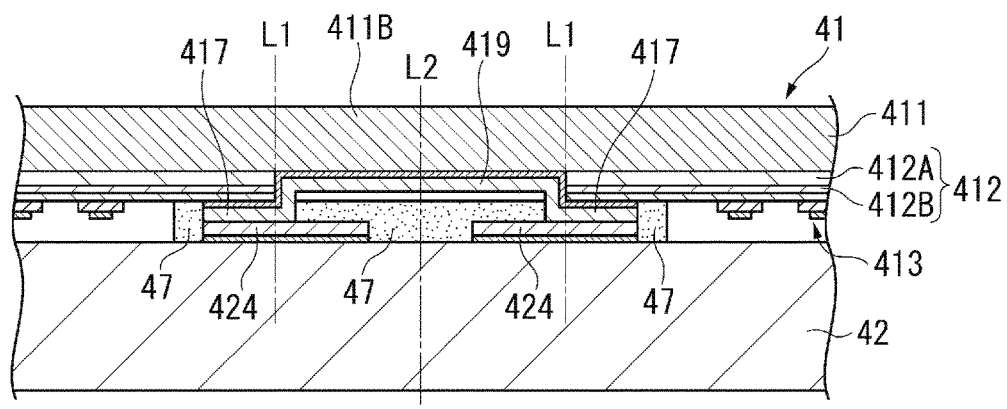
FIG. 17 is a diagram showing the state of the ultrasonic device in an element substrate processing step.

Then, the element substrate 41 and the reinforcing plate 42 are bonded to each other by performing alignment so that the bonding regions Ar2 of the element substrate 41 and the reinforcing plate 42 match each other and that the first lower connection electrode 417 of the element substrate 41 is in contact with the corresponding second lower connection electrode 424 of the reinforcing plate 42 and the first upper connection electrode 418 of the element substrate 41 is in contact with the corresponding second upper connection electrode 425 of the reinforcing plate 42 (refer to FIG. 17). As a result, in the bonding region Ar2, the first lower connection electrode 417 and the second lower connection electrode 424 are electrically connected to each other, and the first upper connection electrode 418 and the second upper connection electrode 425 are electrically connected to each other. In the bonding step S3, for example, after a predetermined time has passed in a state in which the element substrate 41 and the reinforcing plate 42 are in contact with each other, the element substrate 41 and the reinforcing plate 42 are heated in a state in which the element substrate 41 and the reinforcing plate 42 are pressed against each other, and an epoxy based adhesive that is the bonding member 47 is cured. In this manner, the bonding member 47 can be disposed so as to surround the array region Ar1. In addition, at a position overlapping the removal portion 411B in the substrate thickness direction, the second lower connection electrode 424 and the second upper connection electrode 425 are covered by the bonding member 47.

Element Substrate Processing Step

Figure 18:
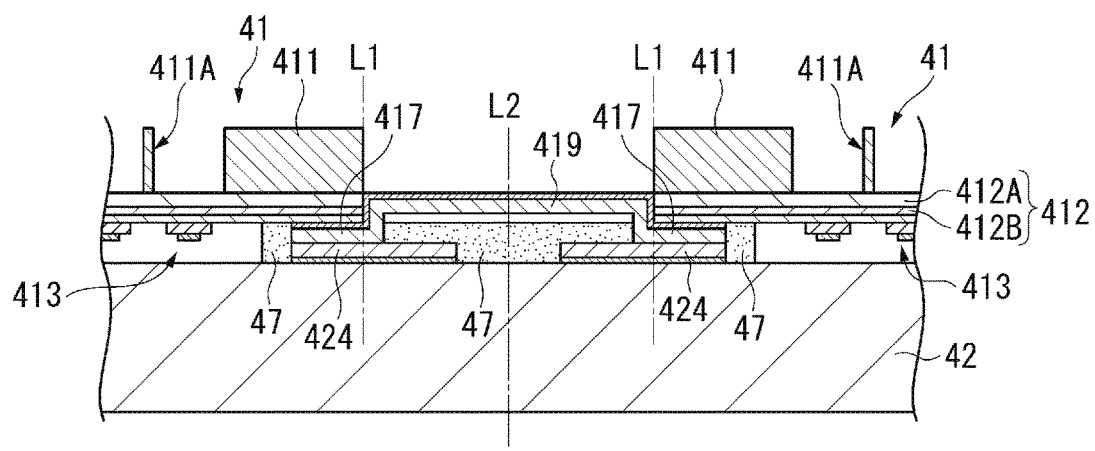
FIG. 18 is a diagram showing the state of the ultrasonic device in the element substrate processing step.

Then, the element substrate processing step S4 is performed. In the element substrate processing step S4, first, as shown in FIG. 18, the substrate body portion 411 is polished so that the thickness of the substrate body portion 411 becomes, for example, 50 μm.

Figure 19:
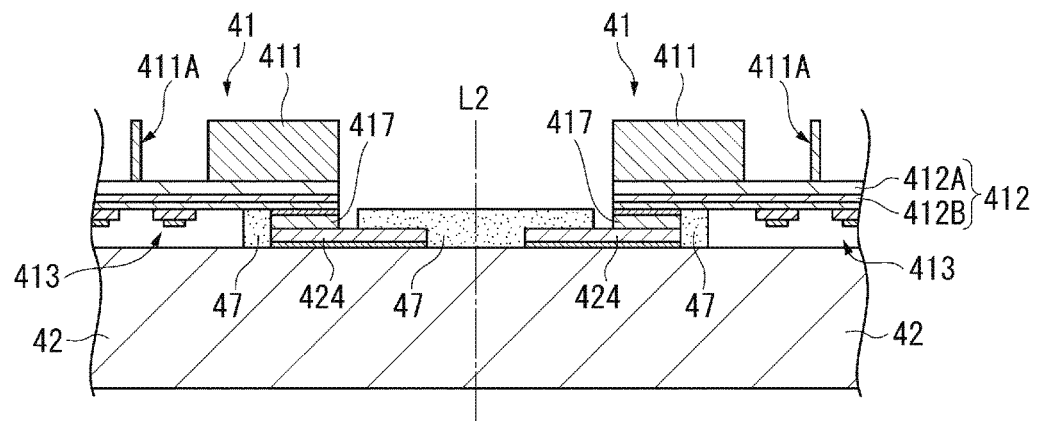
FIG. 19 is a diagram showing the state of the ultrasonic device in the element substrate processing step.

Then, as shown in FIG. 19, the opening 411A is formed in the element substrate 41, and the removal portion 411B is removed. Specifically, on the surface of the substrate body portion 411 not facing the vibration film 412, a mask is formed at the formation position of the opening 411A and a position other than on the removal portion 411B. Then, the opening 411A is formed and the removal portion 411B is removed by wet etching. For example, in a case where the removal portion 411B is an Si substrate, the removal portion 411B is selectively removed by wet etching using KOH as an etchant, and then the mask is removed. In this case, in a plan view as viewed from the substrate thickness direction, at a position overlapping the opening 411A, the support layer 412A formed of $SiO_2$ functions as an etching stopper layer. In addition, at a position overlapping the removal portion 411B, the metal layer 419 functions as an etching stopper layer.

Figure 20:
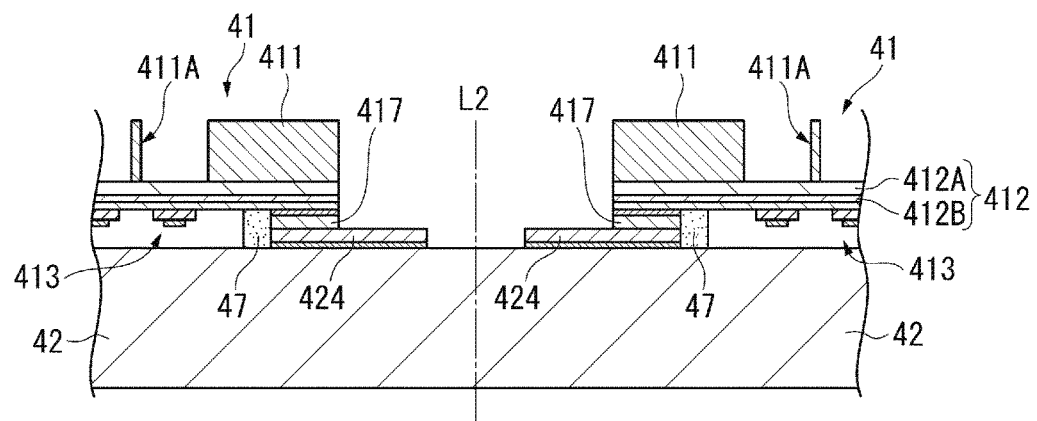
FIG. 20 is a diagram showing the state of the ultrasonic device in a reinforcing plate processing step.

Then, as shown in FIG. 20, the metal layer 419 is removed by etching. In the present embodiment, in the bonding step S3, the bonding member 47 formed of epoxy based adhesive covers the second lower connection electrode 424 and the second upper connection electrode 425. Therefore, at the time of wet etching of the metal layer 419, it is possible to suppress the deterioration of the second lower connection electrode 424 and the second upper connection electrode 425 using an etchant.

In the present embodiment, in the first connection electrode forming step S14, the metal layer 419 is formed along the removal portion 411B. Therefore, it is possible to suppress the degradation of the piezoelectric performance of the piezoelectric element 413, deterioration of the reinforcing plate 42, and the like due to an etchant permeating into the ultrasonic device 22 when removing the removal portion 411B.

In addition, in the case of using the support layer 412A formed of $SiO_2$ as an etching stopper layer without replacing the support layer 412A formed along the removal portion 411B with the metal layer 419, it is possible to suppress the deterioration due to the etchant as described above, but it is necessary to further perform, for example, a step of laser-cutting the support layer 412A in order to remove the support layer 412A. For this reason, manufacturing efficiency is reduced. In contrast, in the case of replacing the support layer 412A with the metal layer 419 as in the present embodiment, it is possible to selectively remove the metal layer 419. Therefore, it is possible to suppress the deterioration of the support layer 412A (vibration film 412) or the reinforcing plate 42. In addition, since the metal layer 419 can be selectively removed by wet etching, it is possible to improve the manufacturing efficiency compared with a case where the support layer 412A is not replaced with the metal layer 419.

Reinforcing Plate Processing Step

Figure 21:
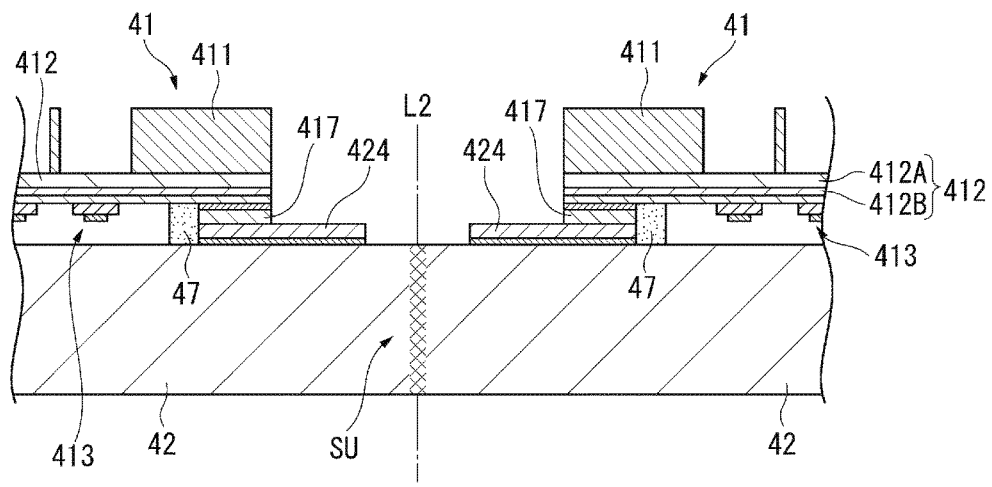
FIG. 21 is a diagram showing the state of the ultrasonic device in a division step.

Then, the reinforcing plate processing step S5 is performed. In the reinforcing plate processing step S5, as shown in FIG. 21, the bonding member 47 that covers the second lower connection electrode 424 and the second upper connection electrode 425 is removed. Specifically, the bonding member 47 is selectively removed by plasma asking using oxygen gas, for example. Thus, the second lower connection electrode 424 and the second upper connection electrode 425 (refer to FIG. 3 and the like) are exposed by the element substrate processing step S4 and the reinforcing plate processing step S5.

Division Step

Figure 22:
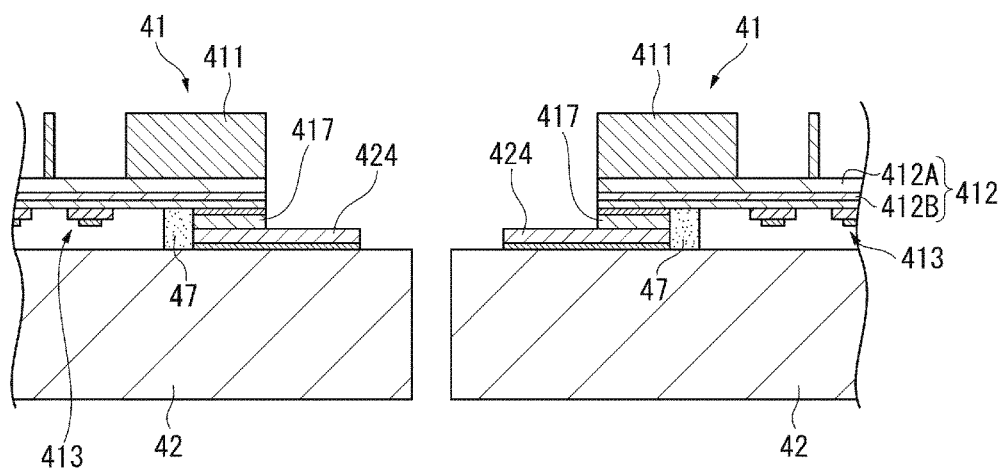
FIG. 22 is a diagram showing the state of the ultrasonic device in the division step.

Then, the division step S6 is performed. In the division step S6, as shown in FIG. 22, a reformulated portion SU is selectively formed within the reinforcing plate 42 along a division line L2 corresponding to the outer peripheral portion of the reinforcing plate 42 by stealth dicing. Specifically, the reformulated portion SU is formed within the reinforcing plate 42 by emitting pulsed laser light along the division line L2 from a laser light source. The reformulated portion SU is a melt and re-solidified layer, and the strength of the reformulated portion SU is lower than the peripheral portion.

Then, the reinforcing plate 42 is divided along the division line L2 where the reformulated portion SU is formed (refer to FIG. 23).

Then, the opening 411A of the substrate body portion 411 is filled with the acoustic matching layer 43, and the acoustic lens 44 is further bonded thereto, thereby manufacturing the ultrasonic device 22 shown in FIGS. 4 and 5 and the like.

Effect of the Embodiment

In the present embodiment, the first lower connection electrode 417 and the first upper connection electrode 418 (hereinafter, also referred to as first connection electrodes 417 and 418) that are connected to the ultrasonic transducer 45 are provided on the element substrate 41 side, and the second lower connection electrode 424 and the second upper connection electrode 425 (hereinafter, also referred to as second connection electrodes 424 and 425) that are connected to the circuit board 23 are provided on the reinforcing plate 42 side. In addition, in the bonding portion 48 between the element substrate 41 and the reinforcing plate 42, the first lower connection electrode 417 and the second lower connection electrode 424 are electrically connected to each other, and the first upper connection electrode 418 and the second upper connection electrode 425 are electrically connected to each other.

In the ultrasonic device 22 configured as described above, since it is possible to pull out an electrode from the element substrate 41 side to the reinforcing plate 42 side in the bonding portion 48, it is possible to mount wiring lines on the lower electrode pad 424P of the second lower connection electrode 424 and the upper electrode pad 425P of the second upper connection electrode 425 that are provided in the reinforcing plate 42. Therefore, since the stress caused by mounting the wiring lines is applied to the reinforcing plate 42, it is possible to suppress the application of the stress to the element substrate 41. As a result, it is possible to suppress the distortion of the element substrate 41.

Here, for example, in a configuration in which a bump electrode is provided in a region (for example, the array region Ar1) other than the bonding portion 48 and the first lower connection electrode 417, and the second lower connection electrode 424 (the first upper connection electrode 418 and the second upper connection electrode 425) are electrically connected to each other, the element substrate 41 is distorted by the pressing force from the bump electrode. Accordingly, there is a possibility that the performance of the ultrasonic transducer 45 will be lowered or the element substrate 41 will be damaged. In particular, in a configuration in which a bump electrode presses, for example, a thin portion (that is, a weak portion of the element substrate 41) where the opening 411A such as the array region Ar1 is formed, in the element substrate 41, the element substrate 41 is likely to be distorted.

In contrast, in the present embodiment, in the bonding portion 48, the first connection electrode 417 and the second connection electrode 424 are electrically connected to each other, and the first connection electrode 418 and the second connection electrode 425 are electrically connected to each other. Therefore, as in a case where a bump electrode is provided, it is possible to suppress the stress applied to the element substrate 41. As a result, it is possible to suppress the lowering of the performance of the ultrasonic transducer 45 or damage to the element substrate 41. In the present embodiment, the bonding portion 48 is a region other than the array region Ar1, more specifically, an outer peripheral portion of the element substrate 41 in a plan view as viewed from the thickness direction, and is formed at a position overlapping a thick portion where the opening 411A is not formed. For this reason, in a thin portion (weak portion) of the element substrate 41, such as the array region Ar1, it is possible to suppress the distortion of the element substrate 41 more reliably compared with a configuration in which the element substrate 41 and the reinforcing plate 42 are electrically connected to each other.

Therefore, according to the present embodiment, it is possible to provide the highly reliable ultrasonic device including the ultrasonic transducer 45 having desired characteristics. In addition, it is possible to provide the ultrasonic probe 2 and the ultrasonic measurement apparatus 1, which are highly reliable, by mounting the ultrasonic device 22.

In addition, the ultrasonic transducer 45 is configured to include the piezoelectric element 413. In such an ultrasonic transducer 45, if the piezoelectric film 415 is distorted according to the distortion of the element substrate 41, there is a possibility that the piezoelectric performance will be lowered. In the present embodiment, since the distortion of the element substrate 41 can be suppressed, it is possible to suppress the lowering of the performance of the ultrasonic transducer 45. Therefore, it is possible to provide the highly reliable ultrasonic device 22.

The element substrate 41 has the substrate body portion 411 and the vibration film 412 that closes the opening 411A formed in the substrate body portion 411. Then, the piezoelectric element 413 is formed on the vibration film 412, the vibration film 412 is vibrated by driving the piezoelectric element 413 so that ultrasonic waves are transmitted, and the vibration of the vibration film 412 when the ultrasonic waves are received is detected by the piezoelectric element 413. In such a configuration, since the strength of the element substrate 41 is reduced, there is a possibility that the element substrate 41 will be easily distorted by the stress. In contrast, in the present embodiment, as described above, in the bonding portion 48, the first connection electrode 417 and the second connection electrode 424 are electrically connected to each other, and the first connection electrode 418 and the second connection electrode 425 are electrically connected to each other. Therefore, even if the strength of the element substrate 41 is reduced as described above, it is possible to appropriately suppress the distortion of the element substrate 41 due to the stress.

In the present embodiment, the piezoelectric element 413 is provided at a position overlapping the opening 411A, on the side of the vibration film 412 not facing the opening 411A. In addition, according to the driving of the piezoelectric element 413, the ultrasonic transducer 45 transmits ultrasonic waves in the +Z direction from the opening 411A, and receives ultrasonic waves incident on the vibration film 412 in the −Z direction.

In such a configuration, by forming the acoustic matching layer 43 within the opening 411A, reflection on the interface between a measurement target and an ultrasonic device is suppressed. Accordingly, a reduction in measurement accuracy is suppressed. On the other hand, if the thickness of the element substrate 41 is large, the depth of the opening 411A is increased. As the thickness of the acoustic matching layer 43 increases, the amount of attenuation of ultrasonic waves is increased. For this reason, there is a possibility that the ultrasonic wave transmission and reception performance will be lowered.

In contrast, in the present embodiment, as described above, it is possible to suppress the stress applied to the element substrate 41 due to wiring mounting. Accordingly, since it is possible to suppress the distortion of the element substrate 41 while reducing the depth of the opening by making the element substrate 41 thin, it is possible to improve the ultrasonic wave transmission and reception performance in the ultrasonic device 22.

The reinforcing plate 42 has the protruding portion 422 protruding from the element substrate 41 when viewed from the thickness direction of the element substrate 41, and parts of the second connection electrodes 424 and 425 are provided in the protruding portion 422. In addition, the second connection electrodes 424 and 425 are connected to the circuit board 23 through the electrode pads 424P and 425P located at both ends of the second connection electrodes 424 and 425 not facing the element substrate 41. In such a configuration, the second connection electrodes 424 and 425 can be pulled out to a position on the reinforcing plate 42 away from the bonding portion 48 between the reinforcing plate 42 and the element substrate 41. Therefore, for example, when making a connection to the circuit board 23 using a wiring material, such as an FPC, it is possible to separate the wiring position from the element substrate 41.

As a result, it is possible to suppress the distortion of the element substrate 41 more reliably.

The bonding portion 48 is disposed so as to surround the array region Ar1. In such a configuration, compared with a configuration in which the element substrate 41 and the reinforcing plate 42 are bonded to each other in a part of the periphery of the array region Ar1, it is possible to firmly fix the element substrate 41 to the reinforcing plate 42. Therefore, it is possible to suppress the distortion of the element substrate 41 more reliably.

In addition, in the present embodiment, in a case where the piezoelectric element 413 is formed on the reinforcing plate 42 side of the vibration film 412, space interposed between the element substrate 41 and the reinforcing plate 42 (space where the piezoelectric element 413 is formed) can be sealed by the element substrate 41, the reinforcing plate 42, and the bonding portion 48 (bonding member 47). Accordingly, since it is possible to suppress the permeation of water into the space where the piezoelectric element 413 is formed, it is possible to suppress the deterioration of the piezoelectric element 413.

In the bonding portion 48, the element substrate 41 and the reinforcing plate 42 are bonded to each other by the bonding member 47 that is an epoxy based adhesive. In such a configuration, since bonding between the element substrate 41 and the reinforcing plate 42 can be easily performed, it is possible to improve the manufacturing efficiency. In addition, since the epoxy based adhesive has water resistance, it is possible to appropriately suppress the deterioration of the piezoelectric element 413 due to permeation of water as described above.

In addition, the ultrasonic device 22 of the present embodiment described above can be manufactured by performing the steps S1 to S6 in the method of manufacturing the ultrasonic device 22. That is, the first connection electrodes 417 and 418 are formed in the bonding region Ar2 of the element substrate 41, and the second connection electrodes 424 and 425 are formed in the bonding region Ar2 of the reinforcing plate 42. In addition, the element substrate 41 and the reinforcing plate 42 are bonded to each other while making the first connection electrode 417 and the second connection electrode 424 in contact with each other and making the first connection electrode 418 and the second connection electrode 425 in contact with each other in the bonding portion 48. Therefore, it is possible to manufacture the highly reliable ultrasonic device 22 as described above.

In the present embodiment, the vibration film 412 formed along the removal portion 411B is removed in the substrate body portion exposure step S13, and the metal layer 419 is formed along the removal portion 411B in the first connection electrode forming step S14. Then, in the element substrate processing step S4, the removal portion 411B and the metal layer 419 are removed.

The removal portion 411B overlaps at least the second connection electrodes 424 and 425 in a plan view as viewed from the substrate thickness direction. Accordingly, it is possible to expose the second connection electrodes 424 and 425 by removing the removal portion 411B and the metal layer 419.

In addition, by removing the removal portion 411B as described above, a plurality of element substrates 41 can be simultaneously formed from a long substrate. Therefore, it is possible to improve the production efficiency.

The metal layer 419 is formed of a metal material different from the material of the substrate body portion 411 or the vibration film 412 of the element substrate 41 or the material of the reinforcing plate 42. Accordingly, it is possible to selectively remove the metal layer 419. Since this is easy, it is possible to improve the production efficiency.

In the present embodiment, in the bonding step S3, when bonding the element substrate 41 and the reinforcing plate 42 to each other using the bonding member 47 that is an epoxy based adhesive, the bonding member 47 is provided at a position where at least the second connection electrodes 424 and 425 are covered in the reinforcing plate 42. In such a configuration, in the bonding step S3, the second connection electrodes 424 and 425 can be covered by the bonding member 47 while bonding the element substrate 41 and the reinforcing plate 42 to each other. Therefore, when removing the metal layer 419 by performing the element substrate processing step S4 after the bonding step S3, the bonding member 47 serves as a protective film of the second connection electrodes 424 and 425, so that the deterioration of the second connection electrodes 424 and 425 can be suppressed.

Modification Examples

The invention is not limited to the embodiments described above, but various modifications, improvements, and appropriate combinations of the respective embodiments may be made in a range where the object of the invention can be achieved.

For example, in the embodiment described above, in a plan view as viewed from the substrate thickness direction, the reinforcing plate 42 has a larger outer size than the element substrate 41. Without being limited thereto, the reinforcing plate 42 may have the same outer size as the element substrate 41, or the reinforcing plate 42 may be smaller than the element substrate 41.

In this case, instead of pulling out the second connection electrodes 424 and 425 to the protruding portion 422 of the reinforcing plate 42 as in the embodiment described above, for example, a configuration may be adopted in which a through electrode is provided in the bonding region of the reinforcing plate 42 and the second connection electrode and the through electrode are electrically connected to each other.

In the embodiment described above, the bonding portion 48 is formed so as to surround the periphery of the array region Ar1. However, the bonding portion 48 may be formed in a part of the periphery of the array region Ar1 without being limited thereto.

In addition, in the embodiment described above, the element substrate 41 and the reinforcing plate 42 are bonded to each other by using the bonding member 47 (for example, epoxy based adhesive) in a part of the bonding portion 48. However, without being limited thereto, a plasma-polymerized film may be formed between the element substrate 41 and the reinforcing plate 42 to bond the element substrate 41 and the reinforcing plate 42 to each other.

In the embodiment described above, the manufacturing method of performing the reinforcing plate forming step S2 after performing the element substrate forming step (step S1) and performing the bonding step (step S3) has been exemplified. However, the element substrate forming step (step S1) may be performed after performing the reinforcing plate forming step S2 without being limited thereto.

In addition, the manufacturing method of forming a plurality of ultrasonic devices 22 simultaneously by performing the element substrate processing step (step S4) and the reinforcing plate processing step (step S5) after performing the bonding process (step S3) has been exemplified. However, the element substrate 41 and the reinforcing plate 42 corresponding to one ultrasonic device 22 may be formed from a long substrate, and the element substrate 41 and the reinforcing plate 42 may be bonded to each other using the same method as in the bonding step S3. Also in this case, it is possible to suppress the distortion of the element substrate 41 by connecting the first connection electrode 417 and the second connection electrode 424 to each other and connecting the first connection electrode 418 and the second connection electrode 425 to each other in the bonding portion 48.

In the embodiment described above, the manufacturing method has been exemplified in which the vibration film 412 formed along the removal portion 411B is replaced with the metal layer 419. However, without being limited thereto, the vibration film 412 formed along the removal portion 411B may be removed using, for example, a laser cutting method after removing the removal portion 411B, instead of replacing the vibration film 412 with the metal layer 419.

In the embodiment described above, the second connection electrodes 424 and 425 are exposed by providing the removal portion 411B at a position overlapping the second connection electrodes 424 and 425 in a plan view as viewed from the thickness direction and removing the removal portion 411B. However, without being limited thereto, for example, the second connection electrodes 424 and 425 may be formed at a position not overlapping the element substrate 41 of the reinforcing plate 42 in a plan view as viewed from the thickness direction. In this case, the removal portion 411B may be set along the outer periphery of the element substrate 41 that is finally formed.

In the embodiment described above, when bonding the element substrate 41 and the reinforcing plate 42 to each other, the bonding member 47 is provided so as to cover the second connection electrodes 424 and 425, so that the bonding member 47 is used as a protective film of the second connection electrodes 424 and 425. However, without being limited thereto, it is not necessary to form the bonding member 47 so as to cover the second connection electrodes 424 and 425. In this case, for example, the element substrate 41 and the reinforcing plate 42 are bonded to each other by the second connection electrodes 424 and 425. However, without being limited thereto, the bonding member 47 may be provided so as to cover only parts of the second connection electrodes 424 and 425, or the bonding member 47 may be formed at a position other than on the second connection electrodes 424 and 425 (for example, periphery of the second connection electrodes 424 and 425) in a plan view as viewed from the thickness direction.

In the embodiment described above, in the division step, the reformulated portion SU is selectively formed within the reinforcing plate 42 by stealth dicing, and the reinforcing plate 42 is divided along the formation position of the reformulated portion SU. However, the invention is not limited thereto. For example, the reinforcing plate 42 may be divided using other methods, such as scribing break or laser cutting.

In the embodiment described above, a configuration has been exemplified in which the vibration film 412 is formed on the back surface side of the substrate body portion 411 where the opening 411A is formed, the piezoelectric element 413 is provided on the back surface side of the vibration film 412 (not facing the opening 411A), and ultrasonic waves are transmitted to the substrate body portion 411 side from the vibration film 412. However, the invention is not limited thereto.

For example, on the vibration film 412 formed on the back surface side of the substrate body portion 411 and on the bottom surface of the opening 411A, the piezoelectric element 413 may be provided.

In addition, a configuration may be adopted in which the vibration film 412 is formed on the opposite side of the back surface of the substrate body portion 411, the piezoelectric element 413 is provided on the side of the vibration film 412 not facing the substrate body portion 411 (opening 411A), and ultrasonic waves may be transmitted from the vibration film 412 to the opposite side of the substrate body portion 411.

In addition, on the vibration film 412 formed on the opposite side of the back surface of the substrate body portion 411 and on the bottom surface of the opening 411A, the piezoelectric element 413 may be provided.

In addition, an example has been illustrated in which the piezoelectric element 413 is formed by a laminate in which the lower electrode 414, the piezoelectric film 415, and the upper electrode 416 are laminated in the thickness direction. However, the invention is not limited thereto. For example, a pair of electrodes facing each other may be disposed on the one surface side of the piezoelectric film 415 perpendicular to the thickness direction. Alternatively, electrodes may be disposed so as to interpose a piezoelectric film therebetween on the side surface along the thickness direction of the piezoelectric film.

In the embodiment described above, as the ultrasonic transducer 45, a configuration including the vibration film 412 and the piezoelectric element 413, which is located on the vibration film 412 and in which the lower electrode 414, the piezoelectric film 415, and the upper electrode 416 are laminated, has been exemplified. However, the invention is not limited thereto. That is, using a piezoelectric element having a bulk-shaped piezoelectric body as an ultrasonic transducer, ultrasonic waves may be transmitted by vibrating the bulk-shaped piezoelectric body instead of the vibration film, or the vibration of the piezoelectric body due to ultrasonic waves may be detected.

As the ultrasonic transducer 45, a configuration may be adopted which includes a substrate body portion, a vibration film disposed opposite to the substrate body portion, a first electrode provided in the substrate body portion, and a second electrode facing the first electrode provided in the vibration film and in which ultrasonic waves are detected by detecting the electrostatic capacitance between a pair of electrodes and ultrasonic waves are transmitted by vibrating the vibration film by applying a voltage between a pair of electrodes. Also in this case, it is possible to suppress the distortion of the element substrate by pulling out an electrode from the element substrate side to the reinforcing plate side in a bonding portion for bonding between the element substrate and the reinforcing plate. In addition, it is possible to suppress the distortion of the element substrate more appropriately by forming a bonding portion in a region other than the array region where an ultrasonic transducer is formed.

Although the ultrasonic measurement apparatus for measuring the living body has been exemplified in the embodiment described above, the invention is not limited thereto. For example, the invention can be applied to an electronic apparatus for detecting defects of various structures or for examining the aging of various structures with the various structures as measurement targets. In addition, for example, the invention can be applied to an electronic apparatus for detecting defects of a measurement target, such as a semiconductor package or a wafer.

In addition, specific structures when implementing the invention may be formed by appropriately combining the embodiments and the modification examples described above in a range where the object of the invention can be achieved, or may be appropriately changed to other structures in a range where the object of the invention can be achieved.

What is claimed is:

1. An ultrasonic device, comprising:
   an element substrate that includes an ultrasonic transducer and a first connection electrode connected to the ultrasonic transducer;
   a reinforcing plate that is bonded to the element substrate to reinforce the element substrate; and
   a second connection electrode provided on the reinforcing plate,
   wherein the first and second connection electrodes are connected to each other in a bonding portion between the element substrate and the reinforcing plate,
   the element substrate has a substrate body portion, in which an opening is formed, and a vibration film provided in the substrate body portion so as to close the opening, and
   the ultrasonic transducer includes a piezoelectric element and the piezoelectric element is provided at a position, which overlaps the opening, on a surface of the vibration film not facing the opening when viewed from a thickness direction of the element substrate.

2. The ultrasonic device according to claim 1, wherein the bonding portion surrounds a region where the ultrasonic transducer of the element substrate is provided.

3. The ultrasonic device according to claim 2, wherein the element substrate and the reinforcing plate are bonded to each other using an adhesive.

4. An ultrasonic device, comprising:
   an element substrate that includes an ultrasonic transducer and a first connection electrode connected to the ultrasonic transducer;
   a reinforcing plate that is bonded to the element substrate to reinforce the element substrate; and
   a second connection electrode provided on the reinforcing plate,
   wherein the first and second connection electrodes are connected to each other in a bonding portion between the element substrate and the reinforcing plate
   wherein the reinforcing plate has a protruding portion that protrudes from the element substrate when viewed from the thickness direction of the element substrate, and
   a part of the second connection electrode is provided in the protruding portion.

5. An ultrasonic probe, comprising:
   an ultrasonic device; and
   a housing in which the ultrasonic device is housed,
   wherein the ultrasonic device includes:
   an element substrate that includes an ultrasonic transducer and a first connection electrode connected to the ultrasonic transducer;
   a reinforcing plate that is bonded to the element substrate to reinforce the element substrate; and
   a second connection electrode provided on the reinforcing plate, and
   the first and second connection electrodes are connected to each other in a bonding portion between the element substrate and the reinforcing plate,
   wherein the element substrate has a substrate body portion, in which an opening is formed, and a vibration film provided in the substrate body portion so as to close the opening, and the ultrasonic transducer includes a piezoelectric element and the piezoelectric element is provided at a position, which overlaps the opening, on a surface of the vibration film not facing the opening when viewed from a thickness direction of the element substrate.

6. An ultrasonic apparatus, comprising:

an ultrasonic device; and a control unit that controls the ultrasonic device, wherein the ultrasonic device includes:

an element substrate that includes an ultrasonic transducer and a first connection electrode connected to the ultrasonic transducer;

a reinforcing plate that is bonded to the element substrate to reinforce the element substrate; and a second connection electrode provided on the reinforcing plate, and the first and second connection electrodes are connected to each other in a bonding portion between the element substrate and the reinforcing plate, wherein the element substrate has a substrate body portion, in which an opening is formed, and a vibration film provided in the substrate body portion so as to close the opening, and the ultrasonic transducer includes a piezoelectric element and the piezoelectric element is provided at a position, which overlaps the opening, on a surface of the vibration film not facing the opening when viewed from a thickness direction of the element substrate.

* * * * *